United States Patent [19]

Aubard et al.

[11] Patent Number: 5,089,639

[45] Date of Patent: Feb. 18, 1992

[54] N-CYCLOALKYLALKYLAMINES, PROCESS FOR THEIR PREPARATION, THEIR USE AS A MEDICAMENT AND THEIR SYNTHESIS INTERMEDIATES

[75] Inventors: Gilbert G. Aubard, Palaiseau; Alain P. Calvet, L'Hay-Les-Roses; Jean-Pierre Defaux, Rueil Malmaison; Claude J. Gouret; Agnès M. Grouhel, both of Meudon; Henry L. Jacobelli, Paray Vieille Poste; Jean-Louis Junien, Sevres; Xavier B. Pascaud, Paris; François F. Roman, Courbevoie, all of France; James P. Hudspeth, Newbury Park; Yuan Lin, Monterey Park, both of Calif.

[73] Assignee: Jouveinal S.A., Paris, France

[21] Appl. No.: 645,405

[22] Filed: Jan. 24, 1991

Related U.S. Application Data

[60] Division of Ser. No. 484,403, Feb. 26, 1990, which is a continuation-in-part of Ser. No. 400,393, Aug. 30, 1989, abandoned.

[30] Foreign Application Priority Data

Sep. 1, 1988 [FR] France ................. 88 11450
Aug. 30, 1989 [EP] European Pat. Off. ........ 89402366.2

[51] Int. Cl.$^5$ .............. C07D 333/20; C07D 307/02; A61K 31/38; A61K 31/34
[52] U.S. Cl. ................. 549/491; 514/925; 514/926; 514/927; 549/74; 549/75; 549/492; 558/390; 558/408; 564/123; 564/161; 564/171; 564/189; 564/190; 564/336; 564/373
[58] Field of Search ................ 549/74, 75, 491, 492; 514/438, 471, 925, 926, 927

[56] References Cited

U.S. PATENT DOCUMENTS 4,695,631 9/1987 Otsuka et al. ................ 544/170

Primary Examiner—Richard L. Raymond
Assistant Examiner—Peter G. O'Sullivan
Attorney, Agent, or Firm—Cushman, Darby & Cushman

[57] ABSTRACT

N-Cycloalkylalkylamines of formula I:

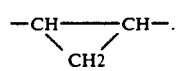

in which:
R1 is phenyl which is optionally mono-, di- or trisubstituted by halogens or lower alkyl, haloalkyl or lower alkoxy radicals, or is an aromatic heterocyclic radical having 5 to 7 chain members, in which the hetero atom is nitrogen, oxygen or sulphur,
R2 is lower alkyl,
R3 is hydrogen or lower alkyl,
m has the value of 1 or 2,
R4 is cycloalkyl —CH(CH2)n, in which a carbon atom may carry a radical Rx, which is lower alkyl or phenyl; and in which n has the values from 2 to 5,
R5 is phenyl, which can be mono-, di- or trisubstituted by halogens or by lower alkoxy radicals, and
Q represents an ethylene-1,2-diyl group —CH=CH— or a cyclopropane-1,2-diyl group $$-CH\underset{CH_2}{\overset{}{\diagdown\diagup}}CH-.$$

7 Claims, No Drawings

N-CYCLOALKYLALKYLAMINES, PROCESS FOR THEIR PREPARATION, THEIR USE AS A MEDICAMENT AND THEIR SYNTHESIS INTERMEDIATES

This is a division of application Ser. No. 07/484,403, filed Feb. 26, 1990 which is a continuation-in-part of application Ser. No. 07/400,393 filed Aug. 30, 1989, now abandoned.

The present invention relates to new N-cycloalkylalkylamines, a process for their preparation and their usefulness in the form of medicaments, as well as their synthesis intermediates.

The amines correspond to the general formula I:

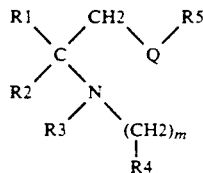

in which:
R1 is phenyl which is optionally mono-, di- or trisubstituted by halogens or lower alkyl, haloalkyl or lower alkoxy radicals, or is an aromatic heterocyclic radical having 5 to 7 chain members, in which the hetero atom is nitrogen, oxygen or sulphur,
R2 is lower alkyl,
R3 is hydrogen or lower alkyl,
m has the value of 1 or 2,
R4 is cycloalkyl —CH(CH2)n, in which a carbon atom may carry a radical Rx, which is lower alkyl or phenyl; and in which n has the values from 2 to 5,
R5 is phenyl, which can be mono-, di- or trisubstituted by halogens or by lower alkoxy radicals, and
Q represents an ethylene-1,2-diyl group —CH=CH— or a cyclopropane-1,2-diyl group

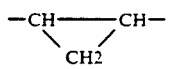

In this description:
by lower alkyl radical there is understood linear or branched radicals containing 1 to 5 carbon atoms,
by halogen there is understood bromine, fluorine and, preferably, chlorine,
by haloalkyl and lower alkoxy there are understood, preferably, the trifluoromethyl and methoxy radicals respectively.

The compounds (I) of the invention contain an asymmetric tetrasubstituted carbon atom adjacent to the amine function, which results in the existence of racemic, laevoratatory and dextrorotatory forms, all the isomers being an integral part of the invention. Moreover, other isomeric structures are possible according to the particular nature of the radicals R1 to R5 and of the group Q or to their combination and are also part of the invention.

The amine function of the compounds I is suitable for the preparation of addition salts with acids, the potential water-solubility of which salts is of use for the preparation of certain medicamentous forms.

The salts of all the compounds I summarized above with therapeutically acceptable inorganic or organic acids are also included in the invention, as are their possible solvates.

As acids which are frequently used for preparation of addition salts there may be mentioned non-limitatively acetic, benzensulphonic, camphosulphonic, citric, ethanesulphonic, fumaric, hydrobromic, hydrochloric, lactic, maleic, malic, methanesulphonic, mucic, nitric, pamoic, phosphoric, salicylic, stearic, succinic, sulphuric and tartaric acids.

When studied on animals, the cycloalkylaklylamines (I) according to the invention and their salts prove to have a low toxicity and at the same time reveal:

a psychotropic activity demonstrated by their ability to inhibit convulsive attacks caused by picrotoxin, an inhibiting activity on amnesia caused by administration of scopolamine, a gastro-duodenal activity as a result of their ability to inhibit the ulcerogenic activity of cysteamine.

The compounds according to the invention in the form of medicaments also prove to have an undeniable usefulness and in this respect preferred compounds are those in which R1 is phenyl, R2 is lower alkyl containing 1 to 3 carbon atoms, and in particular is ethyl, R3 is methyl, R4 is cycloalkyl CH(CH2)n, which is unsubstituted and in which n has a value of 2 to 5, R5 is phenyl and Q is the ethylene-1,2-diyl group —CH=CH—.

More particularly preferred compounds are: α-cinnamyl-N-cyclohexylmethyl-α-ethyl-N-methyl-benzylamine, α-cinnamyl-N-cyclopropylethyl-α-ethyl-N-methyl-benzylamine, α-cinnamyl-N-cyclopropylmethyl-α-ethyl-N-methylbenzylamine, and in particular for activities associated with affinity for sigma receptors its enantiomer of which the hydrochloride is dextrorotatory, and α-cinnamyl-N-cyclobutylmethyl-α-ethyl-N-methyl-benzylamine.

The invention also relates to a process for the preparation of the amines (I) which comprises:

for preparation of a compound (II) of the general formula (I) in which R3 is hydrogen and R1, R2, m, R4, R5 and Q have the abovementioned meanings, i) acylation of an amine (V) of the formula:

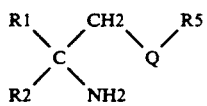

in which R1, R2, R5 and Q are as defined above, with a reagent (VI)

$$(R4-[CH2]m-1]-CO)pZ1 \qquad VI$$

in which:
R4 and m have the meanings defined above,
p has the value 1 or 2 and
Z1 is hydroxyl (—OH) or halogen, such as chlorine or bromine, if p=1, and is an oxygen atom if p=2, to give an intermediate carboxamide (IV)

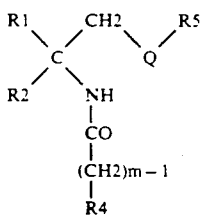

which is reduced by a metal hydride into a cycloalkylalkylamine (II) of the general formula (I) in which R3 is hydrogen

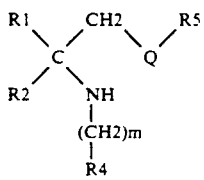

ii) alkylation of an amine (V) by an alkyl halide R4—(CH2)m—Z2 in which R4 and m have the meanings already given and Z2 is a halogen, such as chlorine, bromine or iodine.

and to prepare a cycloalkylalkylamine (III) of the general formula (I) in which R3 is lower alkyl and R1, R2, m, R4, R5 and Q have the meanings already given, i) reductive alkylation on a compound (II) according to the invention which comprises reaction of an aldehyde R6—CHO, in which R6 is the carbon homologue immediately below the radical R3 to be introduced (R3═CH2—R6) and a reducing agent, such as a metal hydride or organometallic hydride, ii) or acylation of an amine (VII)

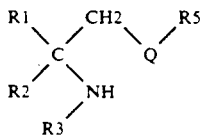

in which R1, R2, R3, R5 and Q have the meanings given for (I), with a halide R4—[(CH2)m—1]COZ4, in which R4 and m have the meanings already defined and Z4 is a halogen, and more particularly chlorine or bromine, to give the intermediate carboxamide (VIII)

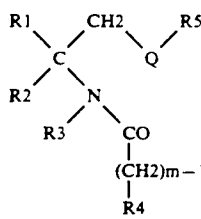

which is reduced by a metal hydride into a cycloalkylalkylamine (III) according to the invention, iii) or reaction of an intermediate aminonitrile (IX)

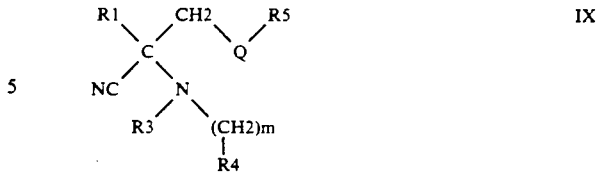

in which R1, R3, m, R4, R5 and Q are as defined for (I), with an organomagnesium reagent R2MgZ3, in which R2 is lower alkyl and Z3 is halogen, such as chlorine, bromine or iodine, to give a cycloalkylalkylamine (III), iiii) or also alkylation of an amine (VII) defined above with an alkyl halide R4—(CH2)m—Z2, in which R4 and m have the meanings defined for (I) and Z2 is a halogen, such as chlorine, bromine or iodine.

As defined, the amines (I) according to the invention differ from the prior art by their chemical structure and also by their use. Thus, L. Miginiac and B. Mauzé in Bull. Soc. Chim. Fr., 1968, (9), p. 3832–44 and Bull. Soc. Chim. Fr., 1973, (5) (Pt. 2), p. 1832–8 report, in the course of a study of the reaction of substituted α-ethylenic organometallic derivatives on aldimines, the preparation of 1-N-methylamino-1,4-diphenylbut-3-ene of the formula C6H5—CH—(NH—CH3)—CH2—CH═CH—C6H5, without indicating a use.

In addition, R. W. Jemison and coll. in J. Chem. Soc., Perkin Trans. I., 1980, p. 1450–7 and 1458–61, in the course of a study of rearrangements of structures involving intermediates of the "ylide" type and catalyses by bases, obtain and describe a product f) on page 1451 and page 1454 which is 1-N,N-dimethylamino-1-(p-nitrophenyl)-4-phenyl-but-3-ene, without indicating a use.

These products differ from the amines according to the invention in the nature of the substitution of their amine function and by the fact that the carbon atom bonded to this function is only trisubstituted, whereas that of the amines (I) also carries an alkyl radical. In addition, no pharmacological activity which can be used therapeutically is reported for these products.

European Patent Application no. 0 298 703 describes thiophene derivatives of the formula:

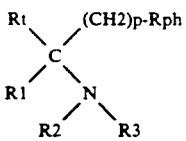

in which, in the widest sense,

Rt is a thienyl radical,
R1, R2 and R3 represent lower alkyl radicals,
Rph is an optionally substituted phenyl radical and
p has the values 1, 2 or 3, and in which, for preferred compounds,
R1 is an ethyl radical,
R2 and R3 are methyl radicals,
Rph is a phenyl, 3,4-dimethoxyphenyl, 3,4,5-trimethoxyphenyl or 4-chlorophenyl radical and
p has the values 1 or 3.

Without objective evidence, the compounds are stated as being of low toxicity and as having a regulatory effect on the motility of the gastrointestinal tract, characterized by a stimulating effect on a tract of reduced activity and, conversely, by an inhibiting effect on a hyperactive tract.

While differing in their chemical structure, in particular in the nature of the carbon chain linking the two aromatic sites and the nature of the substituents of the amine function, the compounds of the European application also differ from the cycloalkylalkylamines (I) according to the invention in their properties. Essentially, no activity of the psychotropic type is reported for the compounds of Application no. 0 298 703, and activity which suggests, amongst other things, the usefulness of the amines (I) in the treatment of neuropsychic conditions.

As has been described above, the intermediate compounds which allow preparation of the products (I) of the invention are essentially derivatives having the structure (V), (VII) and (IX).

The process for the preparation of the compounds (V) comprises alkylation of a compound (XVII) R1—CH2—W, in which R1 is as defined for (I) and W is a nitrile (—CN) or carboxyl (—COOH) radical, with an alkyl halide of the formula R2Z6, R2 being as defined for (I) and Z6 being a halogen, to give, for W=—COOH, an acid of the formula (XV) R1(R2)—CH—COOH, and, for W=—CN, to give a nitrile of the formula (XVI) R1(R2)—CH—CN, which is hydrolyzed into the acid (XV), and then alkylation of the acid (XV) by a reagent (XIII) of the formula Z5—CH2—Q—R5, Z5 being a halogen or an alkylsulphonyloxy radical and R5 and Q being as defined for (I) to give the acids (XIV) R1(R2)C(COOH)CH2—Q—R5, and then preparation, by a Curtius reaction on these acids, of the isocyanates (X)

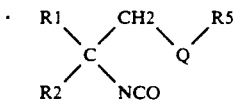   X in which R1, R2, R5 and Q have the meanings given for (I), and finally hydrolysis of their isocyanate function to give the compounds (V).

More precisely, the preparation of an intermediate (V) comprises:

i) Either monoalkylation by an alkyl halide R2—Z6 in which Z6 is halogen, of an acid R1—CH2—COOH (XVII) to give an acid (XV): R1—(R2)CH—COOH, and then a second alkylation with a reagent (XIII) to give the dialkylated acid (XIV) of the formula:

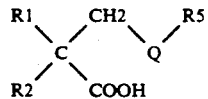   XIV

The alkylation reactions are carried out by known methods, such as those described in "Advanced Organic Chemistry" J. March, 3rd ed. (Wiley) p. 421, which comprise alkylation of the anions of acids obtained by reaction of strong bases on the acids or their salts.

The strong bases used for this purpose can be metallic or organometallic derivatives of alkali metals.

Thus, to give the acids (XV) and if R1 does not contain a substituent of a halogenated nature, such as chlorine atoms or trifluoromethyl radicals, the preparation comprises utilization of the method described in "Journal of Organic Chemistry" 32, 9, p. 2797-2803, 1967, which comprises preparation, in solution in tetrahydrofuran of the dianion of the acid (XVII) by the action of sodium naphthalenate, and then reaction of a halide, which is preferably an iodine derivative, to give the acid (XV), and then the second alkylation of this acid with the derivative (XIII) according to a method prompted by that described in "Tetrahedron Lett." 1980, 21 (12) p. 1169-72, which essentially comprises the use of lithium N,N-diisopropylamide (LDA) to form the reactive dianion.

More precisely, the first alkylation comprises preparation first of the sodium naphthalenate in an anhydrous ethereal medium, such as in THF, by addition of 0.9 to 1.1 mol sodium per mol naphthalene in solution in 0.5 to 1 l THF, and then allowing the reaction to proceed for 4 to 24 h, and more advantageously 12 to 18 h, and addition of this solution to another solution of THF containing 0.3 to 0.5 mol of the acid (XVII) in order to for the reactive dianion by contact for 1 to 24 h at a temperature between 10° and 50° C. The reaction is usually complete after between 3 and 5 h at 20° C., and 0.3 to 1.2 mol halogenated derivative of R2—Z6, and more precisely 0.45 to 0.75 mol of this derivative where the halogen Z6 is iodine, are then introduced. The reaction has ended after stirring for between 1 and 48 h at a temperature between 10° and 50° C. More advantageously, the mixture is kept at 20°-30° C. for 16 to 20 h before being processed to give the intended purified compound (XV).

This compound is then used in the second alkylation reaction, which comprises preparation "in situ" of the LDA from equimolecular amounts of diisopropylamine and butyllithium and then, per mol of LDA thus prepared, addition of 0.5 to 0.3 mol acid (XV) into the THF to give its dianion. The derivative (XIII) is then introduced at a temperature between −10° and 50° C. and the mixture is then allowed to react for 2 to 48 h, according to the reactivity of the compounds.

Thus, preferably, 0.95 to 1 mol butyllithium and then 0.4 to 0.5 mol acid (XV) in solution in about 250 ml THF are added at about −20° C. to one mol diisopropylamine in 500 ml THF. After reaction for 1 to 2 hours at between 20° and 100° C. to form the dianion, the mixture is cooled to about 0° C. and 0.4 to 0.5 mol derivative (XIII) is added.

The reaction proceeds for 1 to 2 h at room temperature and the mixture is then processed to isolate and purify the derivative (XIV) obtained.

ii) Alternatively monoalkylation of a substituted acetonitrile R1—CHS—CN (XVII) by an alkyl halide R2—Z6 described above to give an alkylated acetonitrile (XVI) of the formula R1(R2)—CH—CN, in which R1 and R2 have the definitions described for (I), and then, by a hydrolysis reaction, preparation of the acid (XV), which is subsequently processed as described above to give the acid (XIV). This preparation is particularly preferred if R1 is a phenyl radical substituted by halogen, such as chlorine, or by lower haloalkyl radicals, such as trifluoromethyl.

For this purpose, the method described in "Il Farmaco" Ed. Sci. XXV (6) 1970, p. 409-421, which comprises reaction of an alkyl halide R2—Z6 with a phenylacetonitrile (XVII) by a reaction using a so-called phase transfer catalyst, by introducing one mol acetonitrile into an aqueous solution of 2.5 to 3 mol of this catalyst, such as benzyltriethylammonium chloride, which is preferred, and then 0.75 to 1 mol of the derivative R2—Z6, in which Z6 is bromine or chlorine, is preferably used.

After reaction for 1 to 48 h, and more usually 3 to 5 h, the mixture is processed and the monoalkylated phenylacetonitrile is purified, generally by distillation under reduced pressure. This nitrile is hydrolyzed, first with hydrobromic acid in an ethanolic medium and then with a concentrated solution of sodium hydroxide as described in the article mentioned, and the second alkylation as described in i) follows, to give the acid (XIV).

iii) Subsequent preparation of the isocyanates (X) by a Curtius reaction on the acids (XIV) prepared as described above in i) and ii).

Various rearrangement methods (Hofman, Curtius and Lossen) allow preparation of isocyanates from compounds derived from acids which are, respectively for the reactions mentioned, the amides, the acids and the hydroxamates.

The process for the preparation of the intermediates (X) preferably utilizes the Curtius reaction, which has been the subject of publications listed, for example, in the section "Organic Name Reactions" p. 21 of "Merck Index" 10th ed. It comprises, starting from an acid, successive preparation of its chloride and then the corresponding azide, and finally thermal decomposition of the latter to give the desired isocyanate.

The method advantageously used enables this sequence of reactions to be realized in a single operation and comprises reaction of the acid (XIV) with sodium azide in a halogenated apolar solvent in the presence of an alkyl or aryl dichlorophosphate, such as ethyl or phenyl dichlorophosphate, and a trialkylamine, such as triethylamine, or an aromatic amine, such as pyridine, which is preferred, and then removal of the solvent and direct rearrangement of the azide formed by the action of heat.

In practice, 1 to 1.75 mol phenyl dichlorophosphate and then 2 to 3.5 mol sodium azide and pyridine in equimolecular amounts are added per mol of acid in solution in 3 to 20 liters methylene chloride. The azide is formed at a temperature between 10° and 40° C. by stirring for 4 to 24 h, depending on the reactivity of the products.

After treatment with water and hydrochloric acid, the methylene chloride is removed by distillation, while adding an inert solvent of boiling point greater than 100° C., which can be used as the solvent for the thermal decomposition reaction of the azide into isocyanate.

More advantageously, an aromatic solvent, such as toluene, is used and the decomposition reaction is carried out at the reflux temperature of this solvent until the evolution of gas has ended, which requires a period of between 30 minutes and 8 hours.

The isocyanate (X) is obtained after evaporation of the solvent and is then purified if appropriate.

iv) Finally hydrolysis of the isocyanate (X) to give the intermediate compounds of the formula (V) according to the invention.

This hydrolysis is generally catalysed by acids or bases, preferably inorganic acids or bases, such as hydrobromic, sulphuric, phosphoric and hydrochloric acids, hydrochloric acid being the preferred acid, or alkali metal or alkaline earth metal hydroxides, the hydroxides of sodium and potassium being preferred. The hydrolysis can be carried out in an aqueous medium or in the presence of a water-miscible solvent which does not react with the reaction components. Ethers, such as dioxanes and more particularly tetrahydrofuran (THF), are preferred, as a mixture with water.

For one mol of the derivative (X) to be hydrolyzed, the reaction is thus carried out by dissolving the products in 0.5 to 10 liters THF, and water is then added in various amounts, depending on the derivative to be hydrolyzed, it being possible for the relative composition of the THF-water mixture (v/v) to vary within ratios of between 5-95 and 95-5.

The acid catalyst, for example hydrochloric acid in the form of a concentrated aqueous solution, is added in an amount of 0.2 to 10.0 mol per mol compound (X), and more generally in an amount of 0.5 to 5 mol.

The reaction medium is then brought to a temperature between 50° C. and the reflux temperature of the solvents, at which it is kept for 2 to 72 h in order to obtain a sufficient amount of the product.

It is usually necessary to carry out the heating for 5 to 24 hours, after which the solvent is removed by distillation, the aqueous residue is treated to isolate the primary amine of the formula (V) formed and the product is finally purified by distillation, crystallization or chromatography, as described in the experimental section of the text.

The process for the preparation of compounds (VII) comprises:

i) To obtain more particularly a compound in which R3 is methyl, reduction of the intermediate isocyanate (X) described above. A metal hydride or organometallic hydride is used as the reducing agent under conditions suitable for specific reduction of the isocyanate function without reducing the group Q if this represents an unsaturated bond —CH═CH—.

For this purpose, lithium aluminum hydride or aluminium hydride, which is preferred, is advantageously used. The reactions are carried out in solvents which are inert towards the reagents used, such as in ethers, such as, for example, diethyl ether, 1,2-dimethoxyethane or tetrahydrofuran (THF), which is preferred.

The reducing agent used, the aluminum hydride, can advantageously be prepared "in situ" from aluminum halides and metal hydrides, such as is described, for example, in "Reduction with complex metal hydrides"—N. G. Gaylord, 1956, Ed. Interscience—p. 6 to 8, 51 to 53.

The reduction reaction in THF on one mol isocyanate (X) thus comprises initial preparation "in situ" of aluminum hydride by reaction of 2.25 to 6 mol lithium aluminium hydride on 0.75 to 2 mol aluminum chloride, these reagents being used in a molecular ratio of about 1 to 3, and then introduction of the isocyanate at a temperature between −10° and +30° C., allowing the reduction reaction to proceed for 1 to 24 h at the same temperature, and then decomposition of the reduced complex obtained and isolation of the N-methylamine of the formula (VII) by the usual methods.

These reductions are generally carried out at a temperature between 10° and 20° C. for 2 to 6 h.

ii) To obtain an amine (VII) in which R3 is inert lower alkyl as described for (I), acylation of an intermediate (V) by a reagent (R7—CO)pZ4, in which R7 is hydrogen or a homologous lower alkyl radical below R3 and Z4 is halogen, such as chlorine or bromine, or is hydroxyl, if p is equal to 1, or Z4 also represents oxygen if p is equal to 2, to give an intermediate (XI)

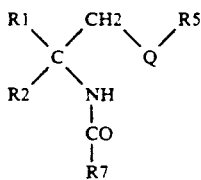

$$\text{XI}$$

the N-carboxamide function of which is reduced by a metal hydride.

iii) Alternatively, alkylation of an intermediate (V) by an alkyl halide R3-Z6, in which Z6 represents chlorine, bromine or iodine.

The process for the preparation of aminonitriles (IX) comprises preparation of an aminonitrile (XII) R1(NC)CH—N(R3)R4 from an aldehyde R1—CHO, a secondary amine HN(R3)—(CH2)m—R4 and an alkali metal cyanide by a Strecker reaction and by a technique described by S. F. Dyke and coll., Tetrahedron 1975, 31, p. 1219, and then alkylation of the derivative (XII) by a reagent Z5—CH2—Q—R5 (XIII), in which R5 has the values defined for (I) and Z5 is chlorine, bromine or iodine or an alkylsulphonyloxy radical.

This alkylation is carried out by first preparing the anion of the aminonitrile (XII) by the action of a suitable organometallic base in an inert solvent, such as THF. Lithium N,N-diisopropylamide (LDA) is preferred. It is prepared "in situ" from equimolecular amounts of N,N-isopropylamine and butyllithium.

After reaction of the compound (XII) for 1 to 2 h at between 20° and 100° C., the reagent (XIII) is added to the anion and the reaction is allowed to proceed for 1 to 2 h at room temperature to give the intermediate (IX), which is purified.

In a manner more explicit than that described above, the preparation of the compounds (II) and (III) according to the invention, which belong to the general formula (I), is described in more detail in the following:

a) When the process comprises acylation of a compound (V) by a reagent (VI) to give an intermediate N-carboxamide (IV) which is then reduced.

If the reagent (VI) is an acid halide (p=1, Z1=halogen), the preferred reaction is carried out in a single-phase medium in toluene or more advantageously methylene chloride, and comprises addition of 1.0 to 1.5 mol amine, which is generally triethylamine, to a solution containing one mol of derivative to be acylated, and then addition of the reagent (VI) in an equimolecular amount to triethylamine. The solution is then kept for 3 to 48 h at a temperature between 15° and 30° C. in order to obtain a reaction which is as complete as possible.

If the acylation reagent (VI) is an acid anhydride (p=2; Z1=oxygen) and if the boiling point of the anhydride is less than 140° C., the reaction can be carried out without a solvent by reaction of the compound (V) in a large excess and at the reflux temperature of the reagent (VI). The preferred method, however, comprises carrying out the reaction using pyridine as the solvent and reacting 1 to 5 mol anhydride per mol of compound to be acylated. The use of 1.2 to 1.8 mol anhydride at the reflux temperature of pyridine for 1 to 3 hours generally leads to suitable results.

The preferred method of acylation of (V) if the reagent (VI) is a carboxylic acid (p=1; m=1 or 2; Z1=OH) comprises preparation in situ of an anhydride, which may be a mixed anhydride, containing the carboxylic acid, and then acylation of the intermediate (V) with this anhydride.

The reaction is advantageously carried out in polar anhydrous solvents of the ether oxide class. Tetrahydrofuran is preferred, and the mixed anhydride is first formed at a temperature between −40° and 0° C. by adding 1.0 to 1.5 mol tertiary amine, such as N-methylmorpholine, and then 0.9 to 1.2 mol isobutyl chloroformate per mol acid (VI).

One mol intermediate (V) to be acylated is then added and the reaction is allowed to proceed for 1 to 48 hours at a temperature between 0° and 60° C.

The result of the reaction is usually satisfactory at a temperature between 10° and 25° C. after a period of 10 to 20 hours.

Alternative methods may employ other dehydrating agents listed, for example, in "Advanced Organic Chemistry", J. March. Ed. Wiley 1985, p. 349. The reaction has thus been carried out with dicyclohexylcarbodiimide as the dehydrating agent in an anhydrous medium, and more particularly with formic acid, and using N,N'-carbonyldiimidazole.

The reduction of the intermediate N-carboxamides is carried out with metal hydrides or organometallic hydrides in a manner suitable for specific reduction of the carboxamide function.

For this purpose, lithium aluminum hydride or aluminum hydride, which is preferred, is advantageously used. The reactions are carried out in solvents which are inert towards the reagents used, such as in ethers, such as, for example, diethyl ether, 1,2-dimethoxyethane or tetrahydrofuran (THF), which is preferred.

Also preferably, the reducing agent used, that is to say the aluminum hydride, can be prepared "in situ" from aluminum halides and metal hydrides, such as is described, for example, in "Reduction with complex metal hydrides"—N. G. Gaylord, 1956, Ed. Interscience—p. 6 to 8, 51 to 53.

The reduction reaction in THF of one mol intermediate (IV) or (VIII) advantageously comprises initial preparation "in situ" of the aluminium hydride by reaction of 2.25 to 6 mol lithium aluminum hydride on 0.75 to 2 mol aluminum chloride, these reagents being used in a molecular ratio of about 1 to 3, and then introduction at a temperature between −10° and +30° C. of the intermediate N-carboxamide, allowing the reduction reaction to proceed for 1 to 24 h at the same temperature, and then decomposition of the reduced complex obtained and isolation of the compounds (II) or (III) according to the invention by the usual methods.

More generally, the reductions are carried out at a temperature between 10° and 20° C. for 2 to 6 h.

As has been described above for the use of the reagent (VI), if this is an acid halide, the reaction can also be applied to acylation of the intermediates (VII) by reagents R4—[(CH2)m—1]—CO—Z4, in which Z4 is chlorine or bromine, for preparation of the intermediate carboxamides (VIII), which, when reduced as described, give the cycloalkylalkylamines (III) according to the invention.

b) If the process comprises N-alkylation of an intermediate (V) or (VII) by an alkyl halide R4—(CH2)m—Z2 already described and in which Z2 is chlorine, bromine or iodine, the reaction is carried out in solvents which are inert towards the reagents, such as, for example, toluene and acetonitrile, by reacting one mol intermediate (V) or (VII) with 0.5 to 1.5 mol halide.

Preferably, 0.80 to 1.20 mol derivative, where the halogen is bromine or iodine, are used and an organic or inorganic base is optionally added to promote the reaction, which comprises heating the reaction medium at a temperature between 20° and 110° C. for 2 to 5 h, the products then being isolated and purified by the usual methods, in particular by chromatography.

c) If the process comprises carrying out reductive N-alkylation to give a compound (III) according to the invention from a compound (II) and an aldehyde R6—CHO, various techniques can be carried out, the essential one of which is described in "Advanced Organic Chemistry", J. March—3rd Ed.—Wiley 1985—p. 798-800.

For the various carbonyl reagents employed, with the exception of formaldehyde, the reaction can advantageously be carried out in a protic anhydrous solvent, such as lower alcohols, such as methanol or ethanol, by reaction of one mol compound II with 1.5 to 10 mol carbonyl compound in the presence of an anhydrous acid catalyst, such as acetic acid or p-toluenesulphonic acid.

The reaction is thus carried out for between 30 minutes and 8 hours at a temperature between that of the laboratory and that of the reflux of the solvent. A reducing hydride of boron, such as sodium borohydride or sodium cyanoborohydride, is then added at room temperature in an amount of 0.5 to 2.5 mol per mol compound (II) employed.

In particular, if the process comprises alkylation of a compound (II) by formaldehyde to give a product (III) according to the invention in which R3 is methyl, the method described in J. Med. Chem. 1982, 25 4, p. 446-51, which comprises reaction in acetonitrile or formaldehyde in aqueous solution in the presence of sodium cyanoborohydride, is advantageously carried out.

d) If the process for preparation of a compound (III) according to the invention comprises reaction of an aminonitrile (IX) with an organomagnesium reagent R2MgZ3, the replacement of the nitrile function by the radical R2 is carried out in accordance with a method prompted by that described by N. J. Leonard and coll., J. Am. Chem. Soc., 1956, 78, p. 1986 and 1957, 70, p. 5279. It is carried out in ethers, such as diethyl ether, methyl t-butyl ether, di-isopropyl or dibutyl ether or tetrahydrofuran, which is preferred, and comprises reaction of 1.5 to 6 mol organomagnesium derivative per mol compound (IX) at a temperature between 5° and 50° C. for 30 minutes to 12 hours.

The method advantageously comprises addition at a temperature between 10° and 20° C. of 1 mol compound (IX), if appropriate in solution in THF, to 4 to 5 mol organomagnesium compound, also in solution in THF. The reaction is continued for 2 to 5 hours at the same temperature and the complex obtained is then decomposed by addition of an aqueous solution of ammonium chloride. After processing, the compound (III) according to the invention is isolated and purified.

As defined, the invention relates to compounds of the general formula (I) in their racemic form and their optically active forms.

The preparation of stereoisomers is carried out:
either by resolution of the racemates of the compounds (II) or (III)
or from optically active precursors, in particular the enantiomeric forms (V), which are themselves prepared by resolution of their racemates.

There are various resolution methods which are listed in works of the scientific literature, such as "Optical resolution procedures for Chemical Compounds" vol. 1—Amines and related compounds—Ed. Paul Newman 1981.

Numerous enantiomers of acid which can allow these resolutions to be carried out from racemic products according to the invention of the structure (II) or (III) or their intermediate (V) are proposed.

The process according to the invention advantageously comprises formation of diastereoisomers of laeverrotatory tartaric acid or of dextrorotatory tartaric acid with the racemic products of the formula (V) in water, and generally, under separation conditions, precipitation of a salt consisting of one of the enantiomers of (V) which has a rotation opposite to that of the tartaric acid used.

The products are purified by repeated crystallization until a constant value of the optical rotation is obtained.

The operating methods which follow illustrate non-limitatively the preparation of intermediate derivatives and compounds (I) according to the invention represented by the products of the formulae (II) and (III).

Depending on the reactions carried out, the compounds are either obtained as such in a satisfactory state of purity, or purified by suitable techniques indicated in the examples, such as crystallization, distillation in vacuo or column chromatography. In this last case, the so-called "chromatoflash" technique on a silica support ("Merck" brand, product silica gel 60, particle size 230 to 400 mesh) is advantageously used.

In addition, the purity, identity and physico-chemical characteristics of the products prepared are reported and determined by:

their boiling point under the vacuum value during their distillation, their melting point, determined by the capillary tube method, the value indicated being uncorrected, thin layer chromatography (TLC) on silica (ready-to-use plates, "Merck" ref. 60 F 254), the technique of which is briefly described:

The products under investigation are deposited on the plate in an amount of about 100 mcg and then eluted in an ascending manner by the solvents or their mixtures which are listed below, the respective proportions being indicated in volumes per volumes:

| ref. | | | |
|---|---|---|---|
| S.A - hexanes | 100/ethyl acetate | 10 |
| S.B - hexanes | 60/ethyl acetate | 10 |
| S.C - hexanes | 40/ethyl acetate | 10 |
| S.D - hexanes | 20/ethyl acetate | 10 |
| S.E - hexanes | 10/ethyl acetate | 10 |
| S.F - methylenechloride | 20/hexane | 80 |
| S.G - methylenechloride | | |
| S.H - methylenechloride | 90/acetone | 10 |
| S.I - methylenechloride | 85/acetone | 15 |
| S.J - methylenechloride | 80/acetone | 20 |
| S.K - methylenechloride | 98/methanol | 2 |
| S.L - methylenechloride | 95/methanol | 5 |
| S.M - methylenechloride | 90/methanol | 10 |
| S.N - methylenechloride | 85/methanol | 15 |
| S.O - methylenechloride | 99/triethylamine | 1 |

After development, the chromatograms are examined under ultraviolet light of 254 nm wavelength and/or color development by spraying with Dragendorff's reagent or tolidine reagent. The Rf values found and the reference elution solvents used are indicated in the examples.

Elemental centesimal analysis, the results of which, which conform to accepted norms which are not reported, are shown to have been carried out by representation of the element analysed.

The proton nuclear magnetic resonants (NMR) is studied at 60 or 90 MHz, the products being dissolved in deuterochloroform. The appearance of signals and their chemical shift, expressed in ppm with respect to the tetramethylsilane used as the internal reference, are indicated. The protons which are called "replaceable" after addition of deuterium oxide are also recorded.

Measurement of the optical rotation is expressed by the specific optical rotation of the products ($\alpha$) under the conditions (concentration, solvent) indicated in the conventional manner.

Finally, various reagents or solvents may be indicated in their usual abbreviated form, amongst other examples THF for tetrahydrofuran.

EXPERIMENTAL SECTION

Preparation of intermediates

A. Intermediates of the formula (XV)

A.1/2-p-Methoxyphenyl-butanoic acid (R1=p—CH3O—C6H4; R2=C2H5)

29.4 g (0.23 mol) naphthalene are introduced into 200 ml THF in a reactor in the absence of moisture and under a nitrogen atmosphere. 5.5 g (0.23 mol) sodium in pieces previously degreased with toluene are added to this solution. A greenish solution is obtained and is stirred for one night.

In addition, 16.6 g (0.10 mol) p-methoxyphenylacetic acid are dissolved in 200 ml THF in another reactor. The sodium naphthalenate solution previously prepared is introduced, while stirring, the mixture is kept for 4 hours at room temperature and about 23.4 g (0.15 mol) iodoethane are then added in the course of about one hour.

After the suspension has been stirred for one night, it is precipitated in 150 ml of a 10% w/v solution of sodium carbonate. The aqueous phase is extracted with ether and the combined organic phases are washed with an N HCl solution and then with a saturated solution of NaCl.

The ether is evaporated and the residue is crystallized in 150 ml petroleum ether.

weight=16.1 g.
y.=83%.
m.p.=64° C.

The intermediate acids A.2, 3 and 4 are prepared by the above operating method starting from substituted phenylacetic acids and suitable alkyl halides.

A.2/3-Methyl-2-phenylbutanoic acid (R1=C6H5; R2=(CH3)2—CH)
y.=67%.
m.p.=70° C.

A.3 / 2-p-Chlorophenyl-butanoic acid (R1=p—Cl—C6H4; R2=C2H5)

81.4 g (0.537 mol) p-chlorophenylacetonitrile are introduced into a solution of 59.2 g (1.48 mol) soda in the form of lozenges in 60 ml water in a reactor at about 5° C., while stirring vigorously, and 1.2 g (52 mmol) benzyltriethylammonium chloride are then added. The mixture is kept for 10 minutes at 5° C. and, after return to room temperature, 50.3 g (0.462 mol) ethyl bromide are then introduced in the course of about 40 minutes at 20° C.

The red-colored mixture is stirred for 4 h and then left for one night at 4° C.

After addition of 560 ml water, the mixture is extracted with benzene. The combined organic phases are washed with a saturated solution of sodium chloride. The benzene is evaporated and the nitrile (XVI) obtained is purified by distillation: b.p./0.05=85°-95° C.
weight=84.0 g.
y.=87%.

0.47 mol nitrile and 21.5 ml absolute ethanol are saturated at −15° C. with a stream of gaseous hydrobromic acid under an anhydrous atmosphere. After one night at room temperature, 880 ml acetone are added and the mixture is then heated and kept at the reflux for one hour. The solution is concentrated on a water bath in vacuo, 800 ml of a 30% w/v concentrated solution of sodium hydroxide are then added to the oily residue and the mixture is stirred under reflux, with agitation, for 30 hours.

The mixture is cooled and extracted with chloroform and the aqueous alkaline phase is acidified in the cold to pH 1 with a concentrated solution of sulphuric acid diluted to half.

After extraction with chloroform and the usual processing of the organic phases, the solvents are evaporated and the residue obtained is crystallized for purification in 300 ml petroleum ether.
weight=60.5 g.
y.=65%.
m.p.=84° C.

A.4 / 2-(m-Trifluoromethyl)-phenyl-butanoic acid (R1=m—F3C—C6H4; R2=C2H5)

The compound is prepared in accordance with the operating method of the above example from m-trifluoromethyl-phenyl-acetonitrile. The following products are obtained:
nitrile XVI: y.=58%.
b.p./0.06=75°-80° C.
acid XV: y.=77%.
m.p.=72° C.

B-Intermediates of the formula (XIV)

B.1 / α-Cinnamyl-α-ethyl-phenylacetic acid (R1=R5=C6H5; R2=C2H5; Q=—CH=CH—)

A solution of 339 g diisopropylamine (3.35 mol) in 2.2 l anhydrous THF is cooled to −10° C. in a reactor of 12 liters in the absence of moisture and under a nitrogen atmosphere. 330 ml of a 10M solution of butyllithium in hexane (3.30 mol) are slowly added at a temperature below −10° C. The solution is kept at this temperature for 30 minutes and a solution of 250 g (1.52 mol) 2-phenylbutanoic acid in 300 ml THF is then added, the temperature being allowed to rise progressively to 15° C. The mixture is then heated at 55°-60° C. for 3 h and cooled to 5° C. and 300 g (1.52 mol) cinnamyl bromide dissolved in 250 ml THF are then introduced, without exceeding 15° C.

The mixture is stirred at the laboratory temperature for 18 h and 2 l 3 N HCl solution and then 1 l water are subsequently added, without exceeding 30° C.; the mixture is extracted with 2 portions 1.5 l ethyl acetate, 4 l hexanes are added to the combined extraction phases and the mixture is washed with 2 portions 1.2 l N NaOH solution. The alkaline aqueous phases are acidified with a concentrated solution of HCl and then extracted with 2 portions 1.5 l ethyl acetate. The combined organic phases are washed with a saturated solution of sodium chloride and then concentrated by distillation.

The crude residual product obtained (428 g) is purified by crystallization in 2 l of a mixture of hexanes-ethyl acetate 3/1 v/v. The product is obtained in the form of fine white crystals.

weight = 320 g.
y. = 75%.
m.p. = 134°-136° C.
TLC: 0.40; S.C.

The alkylation of α-methyl-phenylacetic acid and 3-methyl-2-phenylbutanoic acid (preparation A.2) with cinnamyl bromide is carried out in accordance with the operating method of the above example and leads to the acids (XIV) B.2 and B.3.

B.2/α-Cinnamyl-α-methyl-phenylacetic acid ($R1 = R5 = C6H5$; $R2 = CH3$; $Q = -CH=CH-$)
y. = 83%.
m.p. = 135° C. (hexanes).
TLC: 0.30 1 S.H.

B.3/α-Cinnamyl-α-isopropyl-phenylacetic acid ($R1 = R5 = C6H5$; $R2 = CH3$; $Q = -CH=CH-$)
y. = 55%.
m.p. = 97° C. (hexanes).
TLC: 0.70; S.H.

The process of example B.1 applied to 1-(3-bromo-1-propenyl)-3,4-dichlorobenzene (intermediate XIII described in C.1) with the intermediate acids (XV) described in A.1, A.3 and A.4 gives the compounds B4 to B6.

B.4/α-(3',4'-Dichloro)cinnamyl-α-ethyl-p-methoxyphenylacetic acid ($R1 = p-CH3O-C6H4$; $R2 = C2H5$; $R5 = 3,4\ Cl2-C6H3$; $Q = -CH=CH-$)
y. = 70%.
m.p. = 135° C. (petr. eth.).
TLC: 0.60; S.J.

B.5/α-(3',4'-Dichloro)cinnamyl-α-ethyl-p-chlorophenylacetic acid ($R1 = p-Cl-C6H4$; $R2 = C2H5$; $R5 = 3,4\ Cl2-C6H3$; $Q = -CH=CH-$)
y. = 70%.
m.p. = 160° C. (petr. eth.).
TLC: 0.60; S.L.

B.6/α-(3',4'-Dichloro)cinnamyl-α-ethyl-(3-trifluoromethyl)phenylacetic acid ($R1 = m-F3C-C6H4$; $R2 = C2H5$; $R5 = 3,4\ Cl2-C6H3$; $Q = -CH=CH-$)
y. = 62%.
m.p. = 96° C. (hexanes).
TLC: 0.40; S.L.

C—Intermediates of the formula (XIII)

C.1  1-(3-bromo-1-propenyl)-3,4-dichlorobenzene ($R5 = 3,4\ Cl2-C6H3$; $Z5 = Br$; $Q = -CH=CH-$)

100.6 g (0.46 mol) 3,4-dichlorocinnamic acid are suspended in 1,700 ml methanol in a reactor in the absence of moisture and under a nitrogen atmosphere.

After addition of 56.6 ml BF3-ether complex (65.3 g, 0.46 mol), the mixture is kept at the reflux for 18 h, while stirring. The solution is evaporated, the residue is taken up in about 1 l methylene chloride and the solution obtained is washed with a saturated solution of sodium carbonate and then with water. After distillation, the residue is purified by crystallization in ethanol. 99.2 g methyl 3,4-dichlorocinnamate are obtained in the form of white crystals.
y. = 93%.
m.p. = 115° C.

300 g of a 1.5M toluene solution of DIBAL-H(R) are added to a solution of 5.0 g (0.24 mol) of the above ester in 540 ml toluene at −40° C. in the course of about one hour under a nitrogen atmosphere. The mixture is kept for 2 h 30 min at −40° C. and, after returning a temperature of about 10° C., 1 liter approximately 2M sulphuric acid solution are then carefully introduced. The toluene phase is separated off and the acid phase is extracted with ether. The combined organic phases are washed with a saturated solution of sodium bicarbonate and then dried over $Na_2SO_4$.

The solvents are removed by distillation and the residue is purified by column chromatography.

Elution by a mixture of methylene chloride-acetone 80/20 and then crystallization in hexane gives 47.9 g (y. = 97%) purified 3,4-dichlorocinnamyl alcohol, m.p. = 64° C.

A solution of 25.1 g (0.29 mol) lithium bromide in 225 ml acetonitrile is introduced into a reactor in the absence of moisture and under a nitrogen atmosphere.

39.3 g (0.36 mol) chlorotrimethylsilane are then added at 40° C. in the course of 30 minutes, while stirring, and, successively, 29.45 g (0.145 mol) 3,4-dichlorocinnamyl alcohol dissolved in 125 ml acetonitrile are subsequently added in the course of 20 minutes.

The mixture is kept under reflux for 16 hours, while stirring, and is then cooled and precipitated in 400 ml ether and 250 ml ice-water. The organic phase is separated off and washed with a saturated solution of sodium bicarbonate and then with a saturated solution of NaCl. The solvents are removed and the crude residual product is purified by distillation.
weight = 35.1 g.
y. = 91%.
b.p./0.1 = 115°-120° C.

C.2/1-(3-Chloro-1-propenyl)-3,4,5-trimethoxybenzene ($R5 = 3,4,5(CH3O)3-C6H2$; $Z5 = Cl$; $Q = -CH=CH-$)

A suspension of 22.0 g (0.58 mol) lithium aluminum hydride in 300 ml THF is slowly introduced into a suspension of 25.7 g (0.193 mol) aluminum chloride in 300 ml ether at a temperature of −10° C. under a nitrogen atmosphere. 73.0 g (0.290 mol) methyl 3-(3,4,5-trimethoxyphenyl)-2-propenoate dissolved in 280 ml THF are introduced at the same temperature in the course of 10 minutes. The mixture is then stirred for 15 minutes, subsequently precipitated in an iced 2.5M solution of sulphuric acid and extracted with ether. The combined organic phases are washed and dried. Evaporation of the solvents leads to 3,4,5-trimethoxycinnamyl alcohol, which is used as such.

A solution of 62.6 g (0.279 mol) of the above alcohol in 500 ml methylene chloride is cooled in an ice-water bath. 20.4 g 4-dimethylaminopyridine, 63.9 g p-toluenesulphonyl chloride and 38.9 ml triethylamine are added. The solution is kept for 1 h at room temperature, while stirring, and then diluted by addition of one liter ether. The suspension is filtered and the organic phase is extracted with a 10% (w/v) solution of copper sulphate, then with a saturated solution of sodium bicarbonate and finally with a saturated solution of sodium chloride. After drying and evaporation of the ether, 47.9 g (71%) orange-yellow oily product which is unstable and is used immediately as such for continuation of the syntheses are obtained.

C.3/trans-1-Mesyloxymethyl-2-phenylcyclopropane ($R5 = C6H5$; $Z5 = CH3-SO2-O$; $Q =$ cyclopropane-1,2-diyl)

A solution of 25.0 g trans-2-phenyl-1-cyclopropanecarboxylic acid (154 mmol) in 100 ml THF is added dropwise to 230 ml (230 mmol) of a solution of borane in THF under a nitrogen atmosphere. The solution is brought to the reflux for 3 hours and 130 ml 2N NaOH solution are then slowly added. The mixture is stirred for 30 minutes and then extracted with ether; the ethereal phases are dehydrated over MgSO4 and then concentrated in vacuo to give the crude product as a residue: 20.8 g. The intermediate trans-1-hydroxymethyl-2-phenylcyclopropane is purified by distillation in vacuo.

weight = 18.2 g.
y. = 80%.
b.p./0.25 = 90°-97° C.

9.2 g (66 mmol) product obtained above and 13.8 ml (99 mmol) triethylamine are dissolved in 100 ml methylene chloride. 5.6 ml (73 mmol) methanesulphonyl chloride are added dropwise at −10° C. under a nitrogen atmosphere. The mixture is stirred at −10° C. for 15 minutes, subsequently washed by extraction with water and cold dilute hydrochloric acid and then with a saturated solution of NaHCO3 and a saturated solution of NaCl, and the extract is then dried over MgSO4 at 0° C.

The solvent is removed by distillation in vacuo at a temperature below 10° C. and the unstable product is dissolved in anhydrous THF and used as such for continuation of the preparations.

C.4/trans-1-Bromomethyl-2-phenylcyclopropane (R5=C6H5; Z5=Br; Q=cyclopropane-1,2-diyl)

61.0 g (0.34 mol) N-bromosuccinimide are added to 300 ml methylene chloride. The suspension is cooled to 0° C. and 29.4 ml (0.41 mol) dimethyl sulphide are added under a nitrogen atmosphere; the mixture is subsequently stirred for 30 minutes and then cooled to −25° C., and a solution of 33.6 g (0.23 mol) trans-1-hydroxymethyl-2-phenylcyclopropane is then added dropwise.

The mixture is stirred at 0° C. for 6 hours and then at 25° C. for 16 hours; after dilution with 250 ml hexanes, the mixture is precipitated in 250 ml iced water. The organic phase is washed with a saturated solution of sodium chloride and then dried over MgSO4. The solvents are removed by distillation in vacuo and the residue is purified by distillation.

weight = 40.8 g.
y. = 85%.
b.p./0.2 = 72° C.

D—Intermediates of the formula (X)

X.1/Isocyanates of the formula (II.1)

The isocyanates (X) described in the preparations D.1 to D.6 which follow are prepared by a Curtius reaction in one stage from the acids of the formula (XIV) described above. Since they are unstable, they are purified by chromatography. They are viscous oils, the purity and identity of which are verified by the analyses already described. In addition, and more particularly, these compounds have a characteristic band of isocyanate functions at 2200-2300 cm$^{-1}$ in infra-red spectrography.

Operating method:

1.0 mol acid (XIV) to be processed, 162.5 g (2.5 mol) sodium azide and 197.75 g (202 ml, 2.5 mol) pyridine are added to 8 liters methylene chloride in a reactor in the absence of moisture. 263.7 g (187 ml, 1.25 mol) phenyl dichlorophosphate are introduced dropwise in the course of 15 minutes, while stirring and at room temperature.

The mixture is stirred at the laboratory temperature for 18 to 20 h and then extracted successively with water and subsequently with 0.1N HCl. The organic phase is dried over sodium sulphate and is filtered and 5 liters toluene are then added to the filtrate; the solution is distilled under normal pressure to remove the methylene chloride. The toluene residue is heated very progressively and kept under reflux for 45 minutes to 2 h until the evolution of gas has ended. After cooling, hexane is added, the mixture is filtered and the solvents are then removed by distillation in vacuo on a water bath. The colored oily residue is purified by chromatography.

D.1/α-Cinnamyl-α-ethyl-benzyl isocyanate (R1=R5=C6H5; R2=C2H5; Q=—CH=CH—)
y. = 94%.
TLC: 0.45-0.55; S.C.
NMR: 0.80 (t, 3H); 2.00 (q, 2H); 2.80 (d, 2H); 6.00 (m, 1H); 6.50 (m, 1H); 7.25 (m, 5H); 7.35 (m, 5H).

D.2/α-Cinnamyl-α-methyl-benzyl isocyanate (R1=R5=C6H5; R2=CH3; Q=—CH=CH—)
y. = 72%.
TLC: 0.50; S.F.
NMR: 1.80 (s, 3H); 2.60-2.85 (m, 2H); 5.80-6.60 (m, 2H); 7.10-7.50 (m, 10H).

D.3/α-Cinnamyl-α-isopropyl-benzyl isocyanate (R1=R5=C6H5; R2=CH(CH3)2; Q=—CH=CH—)
y. = 95%.
TLC: 0.80; S.F.
NMR: 0.80 (d, 3H); 1.20 (d, 3H); 2.00-2.50 (m, 1H); 3.00 (d, 2H); 5.50-6.70 (m, 2H); 7.00-7.70 (m, 10H).

D.4/α-(3',4'-Dichloro)cinnamyl-α-ethyl-p-methoxybenzyl isocyanate (R1=p—CH3O—C6H4; R2=C2H5; R5=3,4 Cl2—C6H3; Q=—CH=CH—)
y. 89%.
TLC: 0.30; S.F.
NMR: 0.80 (.., 3H); 2.00 (1, 2H); 2.75 (d, 2H); 3.80 (s, 3H); 5.70-6.45 (m, 2H); 6.80-7.35 (m, 7H).

D.5/α-(3',4'-Dichloro)cinnamyl-α-ethyl-p-chlorobenzyl isocyanate (R1=p—Cl—C6H4; R2=C2H5; R5=3,4 Cl2—C6H3; Q=—CH=CH—)
y. = 87%.
TLC: 0.50; S.F.
NMR: 0.80 (t, 3H); 1.95 (q, 2H); 2.75 (d, 2H); 5.70-6.45 (m, 2H); 6.90-7.60 (m, 7H).

D.6/α-(3',4'-Dichloro)-cinnamyl-α-ethyl-m-trifluoromethylbenzyl isocyanate (R1=m—F3C—C6H4; R2=C2H5; R5=3.4 Cl2—C6H3; Q=—CH=CH—)
y. = 86%.
TLC: 0.40; S.F.
NMR: 0.85 (t,3H); 2.05 (q,2H); 2.80 (d,2H); 5.70-6.45 (m,2H); 6.95-7.70 (m,7H).

E—Intermediates of the formula (V)

E.1.: α-Cinnamyl-α-ethyl-benzylamine (R1=R5=C6H5; R2=C2H5; Q=—CH=CH—)

58.0 g (0.209 mol) of the precursor α-cinnamyl-α-ethyl-benzyl isocyanate described in D.1 are added to a mixture of 1.5 l tetrahydrofuran, 0.2 l water and 50 ml concentrated hydrochloric acid (d=1.19). The stirred solution is heated under reflux for 18 hours.

After cooling, the THF is removed by distillation in vacuo on a water bath. 200 ml water are added to the residue and the mixture is rendered alkaline in the cold to pH 10 by addition of concentrated sodium hydroxide solution and then extracted by taking up three times with 150 ml ether. The ethereal phases are combined, washed with water and then dehydrated over magnesium sulphate.

The ether is removed by distillation and the orange-colored oily residue (54.8 g) is purified by distillation in vacuo. The product is obtained in the form of a colorless viscous oil.

b.p./0.01 = 135°-150° C.

weight = 38.0 g.
y. = 72%.
TLC: 0.15–0.20; S.C.
NMR: 0.70 (t, 3H); 1.45 (s, 2H rep. D20); 1.80 (m, 2H); 2.60 (m, 2H); 6.00 (m, 1H); 6.45 (m, 1H); 7.10–7.55 (m, 10H).

E.2a): (+) α-Cinnamyl-α-ethyl-benzylamine (R1 = R5 = C6H5; R2 = C2H5; Q = —CH=CH—)

4.0 liters demineralized water are introduced into a 6 liter reactor and are heated under reflux, while stirring. 213.0 g (0.487 mol) (±)-α-cinnamyl-α-ethyl-benzylamine of the preceding example E.1 are subsequently added, followed by 139.8 g (0.932 mol) l-(—)-tartaric acid. The mixture is kept under reflux for 30 minutes and then filtered hot over a Buchner filter.

The slightly cloudy solution is left for one night for crystallization.

The precipitate formed is filtered off and dried to constant weight in vacuo at 60° C. 127.0 g product are obtained. The filtrate is kept for processing.

The product is recrystallized in 1.3 l demineralized water under reflux. After standing for one night, the precipitate is filtered off and then dried in vacuo. 115.7 g product are obtained. The second filtrate is also kept.

Recrystallization is carried out in the same manner as above: 92.4 g product (0.230 mol) are obtained. The third filtrate is also kept.

Optical purity of the products:

Samples of the purified insoluble material and of the second and third crystallization filtrate are treated with a sodium hydroxide solution and then extracted with ether. After evaporation of the ether, the specific optical rotation of the residues is determined by polarimetry.

Results

Filtrate of the second crystallization: $[\alpha]_D^{25} = +12.3°$ (c = 6.33; MeOH).

Filtrate of the third crystallization: $[\alpha]_D^{25} = +36.9°$ (c = 6.40; MeOH).

Precipitate of the third crystallization: $[\alpha]_D^{25} = +40.0°$ (c = 6.26; MeOH).

The precipitate obtained after the third crystallization is considered to be of satisfactory optical purity:
weight = 92.4 g.
m.p. = 158° C.
y. = 54.3%.
Anal. Cl8H21N, C4H6O4) C, H, N, O The product is added to 1 liter water.

The mixture is rendered alkaline without exceeding 25° C. by addition of sodium hydroxide and then extracted with ether. The ethereal phases are washed and dried over Na2SO4 and evaporated. The dextrorotatory intermediate product (V) is obtained in the form of a pale yellow oil.
weight = 55.5 g.
y. = 96%.
$[\alpha]_D^{25} = +40.0°$ (c = 6.26; MeOH).
NMR (base): 0.70 (t, 3H); 1.45 (s, 2H rep. D20); 1.80 (m, 2H); 2.60 (m, 2H); 6.00 (m, 1H); 6.45 (m, 1H); 7.10–7.55 (m, 10H).

E.2b: (—)-α-Cinnamyl-α-ethyl-benzylamine (R1 = R5 = C6H5; R2 = C2H5; R3 = R4 = H; Q = —CH=CH—)

The filtrate obtained in the first crystallization of the product E.2a) above is rendered alkaline with a concentrated sodium hydroxide solution and then extracted with 3 portions of 500 ml ether. The combined ethereal phases are washed with a saturated solution of sodium chloride and then dehydrated over Na2SO4. The ether is removed by distillation.
Weight of the residue: 135.0 g.
$[\alpha]_D^{25} = 20.6°$ (c = 5.7; MeOH).

The product is introduced under reflux into 2.3 l water, and 88.7 g (0.59 mol) d-(+)-tartaric acid are added. After dissolution and filtration to remove mechanical impurities, the solution is left for one night.

The precipitate formed is filtered and dried at 60° C. in vacuo. Weight: 149.0 g. The filtrate of the first crystallization is kept.

The insoluble material is recrystallized in 1.5 l water under reflux; after leaving to stand for one night, the precipitate is filtered off and dried. Weight: 127.0 g. The filtrate is kept.

Optical purity of the product.

The procedure is the same as described above with a sample of the filtrates of the first and second crystallization and also with the product obtained after the second crystallization.

Results

Filtrate of the first crystallization: $[\alpha]_D^{25} = +18.0°$ (c = 6.30; MeOH).

Filtrate of the second crystallization: $[\alpha]_D^{25} = -23.0°$ (c = 6.10; MeOH).

Precipitate of the second crystallization: $[\alpha]_D^{25} = -39.3°$ (c = 5.5; MeOH).

This last product is considered to be of satisfactory optical purity and comparable to that of the dextrorotatory isomer obtained above.
weight: 127.0 g.
m.p. = 158° C.
y. = 74.7%.
Anal. (Cl8H21N, C4H6O4) C, H, N, O.

The tartrate is added to 1.5 liters water and, at a temperature below 25° C., the mixture is rendered alkaline by a concentrated sodium hydroxide solution and then extracted with ether. The combined ethereal phases are treated, and after evaporation the laevorotatory product (V) is obtained in the form of a pale yellow oil.
weight = 75.0 g.
y. = 94%.
$[\alpha]_D^{25}$ (base) = -39.3° (c = 5.5; MeOH).
NMR (base): 0.70 (t, 3H); 1.45 (s, 2H rep. D20); 1.80 (m, 2H); 2.60 (m, 2H); 6.00 (m, 1H); 6.45 (m, 1H); 7.10-7.55 (m, 10H).

F—INTERMEDIATES OF THE FORMULA (VII)

F.1/(—)-α-Cinnamyl-α-ethyl-N-methyl-benzylamine (R1 = R5 = C6H5; R2 = C2H5; R3 = CH3; Q = —CH=CH—)

182 ml anhydrous THF, 7.7 g (0.167 mol) pure formic acid and 26.6 g (0.164 mol) 1,1'-carbonyldiimidazole are introduced into a reactor in the absence of moisture and under a nitrogen atmosphere.

The solution is stirred at room temperature for one hour and 40.0 g (0.159 mol) (+)-α-cinnamyl-α-ethyl-benzylamine obtained in E.2a are then added in solution in 430 ml anhydrous THF.

The introduction is carried out in the course of 15 minutes at room temperature, and stirring is then continued for 4 hours.

The THF is removed by distillation in vacuo on a water bath and the residue is taken up in 300 ml N HCl solution. The mixture is extracted with ether and the acid phase is discarded.

The ethereal phase is extracted with a saturated solution of sodium bicarbonate and then water and finally dehydrated over Na₂SO₄. The ether is concentrated to a residual volume of 200 ml. This residual ethereal solution is kept for 24 h at 4° C.

The crystalline insoluble material which precipiates is (+)-α-cinnamyl-α-ethyl-N-formyl-benzylamine (intermediate XI; R1=R5=C6H5; R2=C2H5; R7=H; Q=—CH=CH—).

It is filtered off and dried to constant weight in vacuo at 60° C.
 weight: 41.0 g.
 m.p.=100° C.
 y.=92.3%.
 $[\alpha]_D^{25}$= +38.5° (c=4.05; MeOH).

25.5 g (0.192 mol) aluminum chloride are introduced into a reactor in the absence of moisture and under a nitrogen atmosphere. The reactor is cooled by a bath of solid carbon dioxide/acetone and 309 ml anhydrous ether are added in the course of about 15 minutes without exceeding 0° C. A solution is obtained, which is kept for 30 minutes at 0° C.

In parallel, 22.3 g (0.587 mol) lithium aluminum hydride are introduced into a reactor, also in the absence of moisture and under a nitrogen atmosphere, and after cooling with a bath of solid carbon dioxide/acetone, 309 ml anhydrous THF are added in the course of about 10 minutes.

The suspension obtained is stirred for 15 minutes at 0° C. and then transferred into the first reactor containing the ethereal solution of aluminum chloride.

The transfer is carried out in the course of 10 minutes at a temperature below 0° C.

After stirring for 30 minutes, 41.0 g (0.147 mol) of the above intermediate in solution in 120 ml anhydrous THF are added in the course of 30 minutes at a temperature of about 0° C.

After returning to 20° C., the reaction mixture is kept under reflux for 2 hours, while stirring.

It is cooled to 0° C. and 47.8 ml of a 10% (w/v) solution of sodium hydroxide are then introduced dropwise, followed by 42 ml water.

The mixture is left for one night and the insoluble material is filtered off over a Buchner filter and washed with THF. The combined filtrates are evaporated in vacuo on a water bath. A crude oily residue is obtained.
 weight: 36.1 g.

The product is purified by chromatography over a silica column. Elution with a mixture of methylene chloride-methanol 98-2 (v/v) gives the purified product in the form of a colorless oil.
 weight: 32.6 g.
 y.=83.5%.
 TLC: 0.45-0.55; S.L.
 $[\alpha]_D^{25}$= −16.4° (c=6.1; MeOH).
 NMR (base): 0.70 (t, 3H); 1.40 (s, 1H rep. D20); 1.80 (q, 2H); 2.20 (s, 3H); 2.70 (d, 2H); 5.75-6.50 (m, 2H); 7.10-7.60 (m, 10H).

F.2/(+)-α-Cinnamyl-α-ethyl-N-methyl-benzylamine (R1=R5=C6H5; R2=C2H5; R3=CH3; Q=—CH=CH—)

An identical procedure to that described in F.1 from 40.0 g (−)-α-cinnamyl-α-ethyl-benzylamine prepared in E.2b gives:

(−)-α-Cinnamyl-α-ethyl-N-formyl-benzylamine (Intermediate XI-R1=R5=C6H5; R2=C2H5; R7=H; Q=—CH=CH—)
 weight: 39.3 g.
 m.p.=101° C.
 y.=88.5%.
 $[\alpha]_D^{25}$= −37.9° (c=5.82; MeOH).

After reduction of 39.0 g (0.140 mol) of this compound as described in F.1, 36.4 g product are subsequently obtained in the crude state and are purified by chromatography over a silica column.
 weight: 31.3 g.
 y.=84.2%.
 TLC: 0.45-0.55; S.L.
 $[\alpha]_D^{25}$= +16.3° (c=5.58; MeOH).
 NMR: 0.70 (t, 3H); 1.40 (s, 1H rep. D20); 1.80 (q, 2H); 2.20 (s, 3H); 2.70 (d, 2H); 5.75-6.50 (m, 2H); 7.10-7.60 (m, 10H).

F.3: (+/−)-α-Cinnamyl-α-ethyl-N-methyl-benzylamine (R1=R5=C6H5; R2=C2H5; R3=CH3; Q=—CH=CH—)

145.0 g (1.09 mol) aluminum chloride are introduced into a 12 l reactor cooled in an ice bath.

900 ml anhydrous THF are added slowly and carefully.

3.2 l of a 1M solution of lithium aluminum hydride (3.2 mol) in THF are added to the deep red solution obtained. The mixture is stirred for 15 minutes and 233.0 g (0.84 mol) α-cinnamyl-α-ethyl-benzyl isocyanate dissolved in 200 ml THF are then added dropwise without exceeding 5° C.

After the introduction, the mixture is stirred for 4 h at the laboratory temperature and then cooled to about 5° C. with an ice bath.

1.8 l methyl t-butyl ether are added and 195 ml of a 10% (w/v) solution of NaOH are then carefully added dropwise. 240 ml water are then added and the mixture is stirred for 16 h at room temperature.

The suspension is filtered over a Buchner funnel in vacuo. The insoluble material is discarded and the filtrate is concentrated by distillation in vacuo on a water bath. The crude residual product is a yellow viscous oil, which is purified by distillation. Purified product: b.p./0.02=135°-150° C., which crystallizes in hexane.
 weight=183.2 g.
 m.p.=54°-56° C.
 y.=82%.
 TLC: 0.45-0.55; S.C.
 NMR: 0.70 (t, 3H); 1.40 (s, 1H rep. D20); 1.80 (q, 2H); 2.20 (s, 3H); 2.70 (d, 2H); 6.00-6.45 (m, 2H); 7.10-7.60 (m, 10H).

The N-methyl benzylamines F.4 to F.8 are prepared in accordance with the operating method of this preparation F.3 from benzyl isocyanates substituted in a suitable manner:

F.4: (+/−)-α-Cinnamyl-α-methyl-N-methyl-benzylamine (R1=R5=C6H5; R2=R3=CH3; Q=—CH=CH—)

From α-cinnamyl-α-methyl-benzyl isocyanate
 y.=78% (chromatography).
 TLC: 0.40-0.50; S.M.
 NMR: 1.45 (s, 3H); 1.55 (s, 1H rep. D20); 2.20 (s, 3H); 2.60 (d, 2H); 5.75-6.50 (m, 2H); 7.15-7.45 (m, 10H)

F.5: (+/−)-α-Cinnamyl-α-isopropyl-N-methyl-benzylamine (R1=R5=C6H5; R2=CH(CH3)2; R3=CH3; Q=—CH=CH—)

From α-cinnamyl-α-isopropyl-benzyl isocyanate
 y.=65%.
 m.p.=62° C. (petr. eth.).
 TLC: 0.70: S.M.
 NMR: 0.75 (d, 3H); 0.85 (d, 3H); 1.45 (s, 1H rep. D20); 1.70-2.10 (m, 1H); 2.30 (s, 3H); 2.85-3.05 (m, 2H); 6.05-6.70 (m, 2H); 7.20-7.60 (m, 10H).

F.6: (+/−)-α-(3',4'-Dichloro)cinnamyl-α-ethyl-N-methyl-p-methoxybenzylamine (R1=p—CH3O—C6H4; R2=C2H5; R3=CH3; R5=3,4 Cl2—C6H3; Q=—CH=CH—)

From α-(3',4'-dichloro)cinnamyl-α-ethyl-p-methoxybenzyl isocyanate
y.=40% (chromatography).
TLC: 0.55; S.L.
NMR: 0.70 (t, 3H); 1.40 (s, 1H rep. D20); 1.60–1.90 (q, 2H); 2.15 (s, 3H); 2.60 (d, 2H); 3.80 (s, 3H); 5.70–6.40 (m, 2H); 6.70–7.40 (m, 7H).

F.7: (+/−)-α-(3',4'-Dichloro)cinnamyl-α-ethyl-N-methyl-p-chlorobenzylamine (R1=p—Cl—C6H4; R2=C2H5; R3=CH3; R5=3,4 Cl2—C6H3; Q=—CH=CH—)

From α-(3',4'-dichloro)cinnamyl-α-ethyl-p-chlorobenzyl isocyanate
y.=86% (crude).
TLC: 0.50 S.L.
NMR: 0.70 (t, 3H); 1.35 (s, 1H rep. D20); 1.80 (q, 2H); 2.20 (s, 3H); 2.65 (d, 2H); 5.70–6.50 (m, 2H); 6.90–7.50 (m, 7H).

F.8: (+/−)-α-(3',4'-Dichloro)cinnamyl-α-ethyl-N-methyl-m-trifluoromethylbenzylamine (R1=m—F3C—C6H4; R2=C2H5; R3=CH3; R5=3,4 Cl2—C6H3; Q=—CH=CH—)

From α-(3',4'-dichloro)cinnamyl-α-ethyl-m-trifluoromethylbenzyl isocyanate.
y.=88% (crude).
TLC: 0.70: S.L.
NMR: 0.75 (t, 3H); 1.40 (s, 1H rep. D20); 1.85 (q, 2H); 2.20 (s, 3H); 2.70 (d, 2H); 5.70–6.45 (m, 2H); 6.95–7.85 (m, 7H).

G—INTERMEDIATE OF THE FORMULA (IX)

G.1: α-Amino-N-cyclopropylmethyl-N-methyl-α-(3',4',5'-trimethoxy)cinnamylphenylacetonitrile (R1=C6H5; R3=CH3; m=1; R4=(CH2)2CH; R5=3,4,5 (CH3O)3—C6H2; Q=—CH=CH—)

1.025 mol n-butyllithium (10M solution/hexanes) are added dropwise at 20° C. to a solution of 1.025 mol diisopropylamine in 1 liter anhydrous tetrahydrofuran in a reactor in the absence of moisture and under a nitrogen atmosphere.

The mixture is kept at 20° C. for 15 minutes. 200.3 g (1.0 mol) α-amino-N-cyclopropylmethyl-N-methyl-phenylacetonitrile dissolved in 200 ml THF are introduced at −72° C., stirring is continued for 1 h 30 min at this temperature and 113.0 g (1.025 mol) 3',4',5'-trimethoxy-cinnamyl chloride dissolved in 500 ml THF are then added. After 20 minutes at −72° C., the mixture is stirred for 1 h at room temperature.

1.5 l of a 10% (w/v) solution of NH4Cl and 750 ml of a mixture of hexanes-ethyl acetate 1-1 (v/v) are then added.

The organic phase is separated off and the aqueous phase is extracted again by the mixture of solvents. The combined organic phases are washed by extraction with a saturated solution of sodium chloride and then dried over MgSO4. The solvents are removed by distillation in vacuo on a water bath. The crude oily product (330.0 g) is purified by crystallization.
weight: 22.7 g.
m.p.=67° C. (hexanes).
y.=55%.
NMR: 2.10–2.35 (m, 4H); 2.45–2.60 (m, 5H); 2.65–3.05 (m, 1H); 3.70 (s, 2H); 3.80 (s, 9H); 5.15–5.65 (m, 2H); 6.10–6.40 (m, 2H); 7.20–7.65 (m, 5H)

G.2: α-Amino-α-cinnamyl-N-cyclopropylmethyl-N-methyl-(2-furyl)acetonitrile (R1=furyl; R3=CH3; m=1; R4=(CH2)2CH; RH=C6H5; Q=—CH=CH—)

Preliminary preparation of the intermediate XII α-amino-N-cyclopropylmethyl-N-methyl-(2-furyl)acetonitrile is carried out starting from 2-furaldehyde, N-methyl-N-cyclopropylmethylamine and sodium cyanide. The oily product obtained is purified by distillation in vacuo b.p./0.1=82°–92° C.

The product is alkylated with cinnamyl bromide in accordance with the operating method described for the above compound G.1. The crude oily product obtained (y.=100%) is used as such in the reaction with the organomagnesium derivative.
NMR: 0.10–0.15 (m, 5H); 2.10–2.45 (m, 2H); 2.55 (s, 3H); 2.90 (d, 2H); 5.70 (t, 1H); 6.35 (d, 1H); 6.85–6.95 (m, 1H); 7.10–7.45 (m, 7H).

G.3: α-Amino-α-cinnamyl-N-cyclopropylmethyl-N-methyl-(2-thienyl)acetonitrile (R1=2-thienyl; R3=CH3; m=1; R4=(CH2)2CH; R5=C6H5; Q=—CH=CH—)

The preliminary intermediate XII is prepared from 2-thiophenecarboxaldehyde, N-methyl-N-cyclopropylmethylamine and sodium cyanide. The α-amino-N-cyclopropylmethyl-N-methyl-(2-thienyl)acetonitrile derivative obtained is used without purification.

The compound is alkylated with cinnamyl bromide in accordance with the operating method of G.1. The maroon oily product obtained (y.=100%) is used as such in the reaction with the organomagnesium derivative.
NMR: 0.10–0.15 (m, 5H); 2.10–2.45 (m, 2H); 2.55 (s, 3H); 2.90 (d, 2H); 5.80 (t, 1H); 6.35 (d, 1H); 6.85–6.95 (m, 1H); 7.10–7.40 (m, 7H).

G.4: α-Amino-α-cinnamyl-N-cyclopropylmethyl-N-methyl-(3-thienyl)acetonitrile (R1=3-thienyl; R3=CH3; m=1; R4=(CH2)2CH; R5=C6H5; Q=—CH=CH—)

The compound is prepared in a manner identical to the preceding product G.3 from 3-thiophenecarboxaldehyde.
NMR: 0.0–0.10 (m, 5H); 2.30 (m, 2H); 2.50 (s, 3H); 3.95 (q, 2H); 5.80 (m, 1H); 6.50 (d, 1H); 7.00–7.50 (m, 8H).

G.5: trans-α-Amino-N-cyclopropylmethyl-N-methyl-α-(2-phenyl-1-cyclopropylmethyl)-(2-furyl)acetonitrile (R1=2-furyl; R3=CH3; m=1; R4=(CH2)2CH; R5=C6H5; Q=cyclopropane-1,2-diyl)

The preliminary preparation of the intermediate XII α-amino-N-cyclopropylmethyl-N-methyl-(2-furyl)acetonitrile is carried out starting from 2-furaldehyde and N-methyl-N-cyclopropylmethylamine as described in the preparation G.2. The alkylation is carried out with trans-1-bromomethyl-2-phenylcyclopropane, the preparation of which is described in C.4, in accordance with the general operating method. The maroon oil obtained is used without purification in the following reaction with the organomagnesium derivative.
NMR: 0.10–0.90 (m, 8H); 1.30–1.80 (m, 1H); 2.20–2.30 (m, 4H); 2.40 (s, 3H); 6.30 (m, 1H); 6.50 (t, 1H); 7.10 (m, 5H); 7.40 (m, 1H).

G.6: trans-α-amino-N-cyclopropylmethyl-N-methyl-α-(2-phenyl-1-cyclopropylmethyl)-(2-thienyl)acetonitrile (R1=2-thienyl; R3=CH3; m=1; R4=(CH2)2CH; R5=C6H5; Q=cyclopropane-1,2-diyl)

From the intermediate described in G.3 and the brominated derivative C.4, the maroon oily product is used in the non-purified form.

NMR: 0.10–1.10 (m, 10H); 2.10–2.40 (m, 3H); 2.60 (s, 3H); 6.75–6.90 (m, 1H); 7.05–7.40 (m, 7H).

G.7: trans-α-Amino-N-cyclopropylmethyl-N-methyl-α-(2-phenyl-1-cyclopropylmethyl)-(3-thienyl-)acetonitrile (R1=3-thienyl; R3=CH3; m=1; R4=(CH2)2CH; R5=C6H5; Q=cyclopropane-1,2-diyl)

From the intermediate described in G.4 and the brominated derivative C.4, the oily product is used in the non-purified form.

NMR: 0.30–1.90 (m, 9H); 2.20 (m, 4H); 2.45 (s, 3H); 6.80–7.50 (m, 8H).

PRODUCTS ACCORDING TO THE INVENTION: EXAMPLES

EXAMPLE 1

α-Cinnamyl-N-cyclopropylmethyl-α-ethyl-benzylamine (II; R1=R5=C6H5; R2=C2H5; m=1; R4=CH(CH2)2; Q=—CH=CH—)

a) 160 ml methylene chloride, 10.0 g (40 mmol) α-cinnamyl-α-ethyl-benzylamine (intermediate V described in preparation E.1) and 5.6 ml (4 g, 40 mmol) triethylamine are introduced in succession into a reaction in the absence of moisture.

3.6 ml (4.16 g, 40 mmol) cyclopropanecarbonyl chloride are introduced in the course of 20 minutes under a nitrogen atmosphere at a temperature below 20° C.

The mixture is kept for 2 h 30 min at 20° C., while stirring, and then extracted in succession with a 10% solution of ammonia, followed by water, and then with a saturated solution of sodium bicarbonate, and finally with water again, and is then dried over Na2SO4.

The solvent is evaporated and the intermediate N-cyclopropylcarboxamide corresponding to (IV) is purified by crystallization in ether.

weight: 10.2 g.
y.=80%.
m.p.=130° C.
TLC: 0.80; S.H.
NMR: 0.40–1.00 (m, 7H); 1.00–1.50 (m, 1H); 1.90–2.30 (m, 2H); 2.80–3.20 (m, 2H); 5.80–6.50 (m, 3H of which 1H rep. D20); 7.00–8.00 (m, 10H).

b) 4.42 g (33 mmol) anhydrous aluminum chloride are introduced into a reactor "a" in the absence of moisture, and 56 ml ether dehydrated over a molecular sieve are then added in the course of about 5 minutes, while cooling with a bath of solid carbon dioxide/acetone. The solution is stirred at 0° C. for 30 minutes.

On the other hand, 3.8 g (100 mmol) LAH are introduced into a reactor "b", also in the absence of moisture and under a nitrogen atmosphere, and after cooling with a bath of solid carbon dioxide/acetone, 50 ml THF dehydrated over a sieve are then added in the course of about 10 minutes without exceeding 0° C. The mixture is stirred at 0° C. for 15 minutes.

The suspension prepared in "b" is introduced at 0° C. in the course of about 30 minutes into the ethereal solution of aluminum chloride of reactor "a".

10.1 g (32 mmol) intermediate N-cyclopropylcarboxamide intermediate dissolved in 56 ml THF are then added at room temperature. The mixture is kept under reflux for 1 hour and, after cooling to 20° C., 6.0 ml of a 10% solution of NaOH and then 7.5 ml water are carefully added.

After stirring for one night, the insoluble material is filtered off and the filtrate is evaporated in vacuo. The crude product is obtained in viscous form (8.8 g). It is purified by chromatography.

weight: 5.0 g.
y.=51%.
TLC: 0.45; S.L.
NMR: 0.00–0.10 (m, 2H); 0.30–0.60 (m, 2H); 0.60–1.00 (m, 4H); 1.60–2.00 (m, 3H); 2.20 (d, 2H); 2.65 (d, 2H); 5.80–6.60 (m, 2H); 7.00–7.70 (m, 10H) of which 1H rep. D20).

Hydrochloride:
y.=82%.
m.p.=200° C. (ether).
Anal. (C22H27N, HCl) C, H, Cl, N.

EXAMPLE 2

α-Cinnamyl-α-ethyl-N-(1-methylcyclopropyl)-methyl-benzylamine (II; R1=R5=C6H5; R2=C2H5; m=1; R4=C(CH2)2CH3; Q=—CH=CH—)

5.0 g (20 mmol) α-cinnamyl-α-ethyl-benzylamine (preparation E.1) are dissolved in 40.0 ml dimethylformamide, dehydrated over a molecular sieve, in a reactor in the absence of moisture.

The following are added in succession to the solution under a nitrogen atmosphere:

2.1 g (21 mmol) 1-methylcyclopropanecarboxylic acid, 2.8 g (21 mmol) hydroxybenzotriazole, 4.3 g (20 mmol) dicyclohexylcarbodiimide, and 11.2 ml anhydrous triethylamine.

The solution is stirred for 24 hours at the laboratory temperature and then evaporated in vacuo on a water bath.

The residue is dissolved in 150 ml ethyl acetate, the solution is extracted with 150 ml of a 10% (w/v) solution of citric acid and the precipitate formed is filtered off. The aqueous phase is discarded. The organic phase is processed and dried over Na2SO4 and the ethyl acetate is removed by distillation. The residue is crystallized in hexane and the insoluble material, which is the corresponding N-carboxamide (IV), is filtered off and dried.

weight: 4.7 g.
y.=70%.
m.p.=100° C.
TLC: 0.45; S.L.
NMR: 0.40–060 (m, 2H); 0.75 (t, 3H); 1.00–1.30 (m, 2H); 1.30 (s, 3H); 1.90–2.30 (m, 2H); 2.70–3.20 (m, 2H); 5.60–6.60 (m, 3H of which 1H rep. D20); 6.90–7.50 (m, 10H).

b) 4.5 g (13.5 mmol) of the above N-carboxamide are reduced as described in b) of example 1.

y.=93% (chromatography).
TLC: 0.80; S.L.
NMR: 0.20 (s, 4H); 0.70 (t, 3H); 1.10 (s, 3H); 1.30 (s, 1H rep. D20); 1.50–1.90 (m, 2H); 2.00–2.30 (m, 2H) 2.65 (d, 2H); 5.70–6.50 (m, 2H); 6.90–7.60 (m, 10H).

Hydrochloride:
y.=85%.
m.p. =212°–214° C. (ether).
Anal. (C23HOCl N.HCl) C, H, Cl, N.

EXAMPLE 3

α-Cinnamyl-α-ethyl-N-(trans-2-phenyl-cyclopropyl)-methylbenzylamine (II; R1=R5=C6H5; R2=C2H5; m=1; R4=C6H5—CH (CH2)CH; Q=—CH=CH—)

The compound is prepared in accordance with the operating method of example 1 from the intermediate V described in preparation E.1 and trans-2-phenyl-1-cyclopropanecarbonyl chloride.

a) Intermediate IV (m=1; R4=C6H5—CH(CH2)CH)
y.=95%.
m.p.=163° C. (hexanes-methylene chloride).
TLC: 0.30–0.40; S.G.

b) Compound II of the example
y.=83% (crude)
TLC: 0.50–0.60; S.K.
NMR: 0.60–1.00 (m, 5H); 1.00–1.95 (m, 5H of which 1H rep. D20); 2.20–2.50 (m, 2H); 2.70 (d, 2H); 5.80–6.60 (m, 2H); 6.90–7.55 (m, 15H).

Hydrochloride:
y.=72%.
m.p.=217° C. (ether).
Anal. (C28H31N, HCl) C, H, Cl, N.

EXAMPLE 4

α-Cinnamyl-N-cyclohexylmethyl-α-ethyl-benzylamine (II; R1=R5=C6H5; R2=C2H5; m=1; R4=CH (CH2)5; Q=—CH=CH—).

a) 340 ml THF dehydrated over a molecular sieve and 7.7 g (60 mmol) cyclohexanecarboxylic acid are introduced into a reactor in the absence of moisture. 7.3 ml (6.7 g—66 mmol) N-methylmorpholine are then added to this solution.

After stirring for 5 minutes, the solution is cooled to −20° C. and 7.8 ml (8.2 g—60 mmol) isobutyl chloroformate and 15.0 g (60 mmol) benzylamine prepared in E.1 are then added in the course of about 30 minutes at −20° C.

The suspension is stirred for 30 minutes at −20° C. and then at room temperature for 16 hours. After concentration by distillation in vacuo until a concentrate of about 250 ml is obtained, 300 ml ether are added and the mixture is extracted successively with a 2N solution of HCl, a saturated solution of NaHCO3 and then a saturated solution of NaCl.

The organic phase is dried and evaporated in vacuo.

The residue of crude product (12.4 g) is purified by chromatography to give the corresponding intermediate (IV) (m=1, R4=CH(CH2)5).
weight:=10.3 g.
y.=48%.
TLC: 0.30; S.G.
NMR: 0.70 (t, 3H); 1.00–2.30 (m, 13H); 2.70–3.20 (m, 2H); 5.50–6.60 (m, 3H of which 1H rep. D20); 7.00–7.60 (m, 10H).

b) The above N-cyclohexylcarboxamide is reduced as described in stage b) of example 1:
y.=70% (chromatography).
TLC: 0.70; S.H.
NMR: 0.70 (t, 3H); 1.00–2.00 (m, 14H of which 1H rep. D20); 2.20 (d, 2H); 2.70 (d, 2H); 5.80–6.50 (m, 2H); 7.00–7.60 (m, 10H).

EXAMPLE 5

α-Cinnamyl-N-cyclopropylethyl-α-ethyl-benzylamine (II; R1=R5=C6H5; R2=C2H5; m=2; R4=CH (CH2)2; Q=—CH=CH—)

a) The corresponding intermediate N-carboxamide (IV; m=(2); R4=CH (CH2)2) is prepared in accordance with stage a) of example 4 above from α-cinnamyl-α-ethyl-benzylamine (preparation E.1) and 2-cyclopropaneacetic acid.
y.=75% (crude).
TLC: 0.80; S.H.
NMR: 0.00–0.30 (m, 2H); 0.40–1.00 (m, 6H); 2.00–2.40 (m, 4H); 2.80–3.10 (m, 2H); 5.70–6.60 (m, 3H of which 1H rep. D20); 7.10–7.60 (m, 10H).

b) The above N-carboxamide is reduced in accordance with operating method b) of example 1.
y.=83%.
TLC: 0.70; S.H.
NMR: 0.00–0.10 (m, 2H); 0.20–0.50 (m, 2H); 0.50–0.90 (m, 4H); 1.10–1.50 (m, 2H); 1.50–2.00 (m, 3H of which 1H rep. D20); 2.30–2.80 (m, 4H); 5.80–6.60 (m, 2H); 7.10–7.60 (m, 10H).

EXAMPLE 6

α-Cinnamyl-α-ethyl-N-methyl-N-(trans-2-phenyl-cyclopropyl)methyl-benzylamine (III: R1=R5=C6H5; R2=C2H5; R3=CH3; m=1; R4=C6H5—CH (CH2)CH; Q=—CH=CH—)

150 ml acetonitrile and 8.5 g (22 mmol) compound II obtained in example 3 are introduced into a reactor. 28.0 ml of a 37% (w/v) solution of formaldehyde (10.36 g—518 mmol) are subsequently added and the mixture is then cooled to 0° C.

4.2 g (67 mmol) sodium cyanoborohydride are then added at this temperature, the mixture is stirred for 5 minutes and 4.2 ml (4.41 g—73 mmol) glacial acetic acid are then added dropwise in the course of about 10 minutes.

The mixture is stirred for one hour at room temperature and 1.4 g (24 mmol) acetic acid are then added successively at the same temperature. These reagents are allowed to act for one hour and identical amounts are the added again.

After a last period of stirring of 3 hours at room temperature, 300 ml ether are added, the aqueous phase is removed and the organic phase is washed by successive extractions with 100 ml 10% NaOH solution, 2 portions of 100 ml water and then 2 portions of 200 ml of a saturated solution of NaCl. The organic phase is dried over Na2SO4 and the solvents are removed by distillation in vacuo.

The crude product obtained (8.0 g) is purified by chromatography (6.08 g) and finally by distillation in vacuo: b.p./0.08=225°-230° C.
weight=4.5 g.
y.=52%.
TLC: 0.80; S.K.
NMR: 0.50–0.90 (m, 5H); 1.00–1.70 (m, 2H); 1.90 (q, 2H); 2.20–2.60 (m, 5H); 2.80 (d, 2H); 6.00–6.60 (m, 2H); 6.90–7.55 (m, 15H).

EXAMPLE 7

α-Cinnamyl-N-cyclohexylmethyl-α-ethyl-N-methyl-benzylamine (II: R1=R5=C6H5; R2=C2H5; R3=CH3; m=1; R4=CH (CH2)5; Q=—CH=CH—)

The compound is prepared from the product of example 4 by reductive methylation with formaldehyde and sodium cyanoborohydride as described in example 7 above.

y.=80% (chromatography).
TLC: 0.60; S.H.
NMR: 0.70 (t, 3H); 1.00–2.00 (m, 13H); 2.20–2.50 (m, 2H); 2.70–3.00 (m, 2H); 6.00–6.60 (m, 2H); 7.10–7.60 (m, 10H).

EXAMPLE 8

α-Cinnamyl-N-cyclopropylethyl-α-ethyl-N-methyl-benzylamine (II; R1=R5=C6H5; R2=C2H5; R3=CH3; m=2; R4=CH (CH2)2; Q=—CH=CH—)

The product is prepared from the compound of example 5 in accordance with the operating method described in example 6.

y.=76% (chromatography).
TLC: 0.70; S.H.
NMR: 0.00–0.10 (m, 2H); 0.20–0.50 (m, 2H); 0.50–0.90 (m, 4H); 1.30 (q, 2H); 1.70–2.00 (m, 2H); 2.25 (s, 3H); 2.40–2.70 (m, 2H); 2.80 (d, 2H); 6.00–6.60 (m, 2H); 7.10–7.60 (m, 10H).

EXAMPLE 9

α-Cinnamyl-N-cyclopropylmethyl-α-ethyl-N-methyl-benzylamine (III.3: R1=R5=C6H5; R2=C2H5; R3=CH3; m=1; R4=(CH2)2CH; Q=—CH=CH—)

13.52 g (0.051 mol) α-cinnamyl-α-ethyl-N-methyl-benzylamine (described in preparation F.3) and 8.5 ml (61 mmol) triethylamine are dissolved in 200 ml methylene chloride in a reactor in the absence of moisture and under a nitrogen atmosphere. 5.5 ml (0.061 mol) cyclopropanecarbonyl chloride are added at room temperature, while stirring.

The mixture is stirred for 24 h at room temperature and then extracted successively with a dilute ammonia solution and a hydrochloric acid solution and then washed with water and dried over MgSO4. After evaporation, the derivative of the formula IV (R3=CH3, m=1, R4=CH (CH2)2) is obtained in the form of a viscous oil with an orange color, and is reduced in the following stage without being purified.

A solution of aluminum hydride in a mixture of THF/ether is prepared from 6.80 g (0.051 mol) aluminum chloride and 5.80 g (0.015 mol) lithium aluminum hydride in a reactor in the absence of moisture and under a nitrogen atmosphere.

The amide obtained above dissolved in 100 ml THF is added to the mixture obtained. The reaction mixture is stirred for 3 h at the laboratory temperature and then diluted by addition of 250 ml ether. 9.2 ml of a 10% (w/v) solution of NaOH and then 10.0 ml water are carefully added dropwise and the mixture is stirred for 16 h. It is filtered, the filtrate is evaporated in vacuo on a water bath and the residue is purified by distillation.

weight: 13.52 g.
b.p./0.02=150°–190° C.
y.=83%.
TLC: 0.70–0.75; S.E.
NMR: 0.10 (m, 2H); 0.30–0.60 (m, 2H); 0.60–1.00 (m, 4H); 1.90 (q, 2H); 2.35 (d, 2H); 2.45 (s, 3H); 2.80 (d, 2H); 6.00–6.50 (m, 2H); 7.10–7.60 (m, 10H).

Hemimaleate:

1.86 g (16 mmol) maleic acid in ethanolic solution are added to an ethereal solution of 4.88 g (15.3 mmol) of the above product. The precipitate which forms in the cold, while stirring, is filtered off and dried.

weight: 5.36 g.
y.=80%.
m.p.=99°–102° C.
Anal. (C23H29N.C4H4O4) C, H, N, O

EXAMPLE 10

(+)-α-Cinnamyl-N-cyclopropyl-methyl-α-ethyl-N-methyl-benzylamine hydrochloride (III; R1=R5=C6H5; R2=C2H5; R3=CH3; m=1; R4=(CH2)2CH; Q=—CH=CH—)

18.9 g (y. 97.7%) of the intermediate N-methyl-N-cyclopropylcarboxamide are obtained in accordance with the operating method of example 10 from 15.4 g (0.058 mol) (−)-α-cinnamyl-α-ethyl-N-methyl-benzylamine (preparation F.1) and 7.28 g (0.070 mol) cyclopropanecarbonyl chloride.

$[\alpha]_D^{25}$ = +92.6° (C=5.94; MeOH).

The product reduced in accordance with the technique of example 10, gives the product, which is purified by column chromatography.

weight: 14.7 g.
y.: 81%.
TLC: 0.70–0.80; S.E.
Anal. (C23H19N) C, H, N.
NMR: 0.10 (m, 2H); 0.30–0.60 (m, 2H); 0.60–1.00 (m, 4H); 1.90 (q, 2H); 2.35 (d, 2H); 2.45 (s, 3H); 2.80 (d, 2H); 6.00–6.50 (m, 2H); 7.10–7.60 (m, 10H).

Hydrochloride:
y.=83%.
m.p.=177° C. (ethyl acet.).
$[\alpha]_D^{25}$ = +49.7° (c=3; methanol).
Anal. (C23H29N, HCl) C, H, Cl, N.

EXAMPLE 11

(−)-α-Cinnamyl-N-cyclopropyl-methyl-α-ethyl-N-methyl-benzylamine hydrochloride (III: R1=R5=C6H5; R2=C2H5; R3=CH3; m=1; R4=(CH2)2CH; Q=—CH=CH—)

When prepared in accordance with example 11 above, from the intermediate prepared in F.2, the corresponding N-methyl-N-cyclopropylcarboxamide is obtained:

y.=94.3%;
$[\alpha]_D^{25}$ = −91.4° (c=5.6% MeOH);
which, when reduced in accordance with the technique of example 10, gives, after purification by column chromatography, the product in the form of a colorless viscous oil.

y.=75%.
TLC: 0.70–0.80; S.E.
Anal. (C23H19N) C, H, N.
NMR: identical to the product of example 10.

Hydrochloride:
y.=78%.
m.p.=177° C. (ethyl acet.).
$[\alpha]_D^{25}$ = 49.5° (c=3.2; methanol).
Anal. (C23H29N, HCl) C, H, Cl, N.

EXAMPLE 12

α-Cinnamyl-N-cyclobutylmethyl-α-ethyl-N-methyl-benzylamine (III; R1=R5=C6H5; R2=C2H5; R3=CH3; m=1; R4=(CH2)CH; Q=—CH=CH—)

When prepared in accordance with the operating method of example 10 above from 15.0 g (0.056 mol) α-cinnamyl-α-ethyl-N-methyl-benzylamine (intermediate F.3) and 8.05 g (0.068 mol) cyclobutanecarbonyl chloride, purification by column chromatography gives 18.0 g (y. 92.5%) of the corresponding intermediate N-methyl-N-cyclobutyl-carboxamide in the form of a viscous oil (TLC: 0.25–0.35; S.G).

The product of 16.5 g (0.0475 mol) is reduced as described in example 10. Purification by column chromatography gives the product in the form of a viscous oil.
weight: 8.5 g.
y.: 53.7%.
TLC: 0.40–0.60; S.H.
NMR: 0.70 (t, 3H); 1.40–2.10 (m, 9H); 2.25 (s, 3H); 2.50 (s, 2H); 2.85 (d, 2H); 6.60–6.60 (m, 2H); 7.10–7.60 (m, 10H).

EXAMPLE 13

α-Cinnamyl-N-cyclopropylmethyl-N-α-dimethyl-benzylamine (I.3; R1=R5=C6H5; R2=R3=CH3; m=1; R4=CH (CH2)2; Q=—CH=CH—)

As described in example 10, the compound is prepared from the intermediate described in F.4 and cyclopropanecarbonyl chloride.
y.=56% (chromatography).
TLC: 0.40; S.C.
NMR: 0.00–0.10 (m, 2H); 0.20–0.55 (m, 2H); 0.55–1.00 (m, 1H); 1.30 (s, 3H); 1.85–2.25 (m, 2H); 2.40 (s, 3H); 2.50–2.80 (m, 2H); 5.50–6.35 (m, 2H); 7.10–7.70 (m, 10H).

EXAMPLE 14

α-Cinnamyl-N-cyclopropylmethyl-α-isopropyl-N-methyl-benzylamine (III; R1=R5=C6H5; R2=(CH3)2CH; R3=CH3; m=1; R4=CH(CH2)2; Q=—CH=CH—)

In accordance with example 10 and prepared from the intermediate described in F.5 and cyclopropanecarbonyl chloride
y.=78% (chromatography).
TLC: 50.35; S.C.
NMR: 0.00–0.10 (m, 2H); 0.30–0.55 (m, 2H); 0.60–0.90 (m, 7H); 2.10–2.60 (m, 6H); 2.90–3.20 (m, 2H); 6.30–6.70 (m, 2H); 7.10–7.70 (m, 10H).

EXAMPLE 15

α-(3',4'-Dichloro)cinnamyl-N-cyclopropyl-methyl-α-ethyl-N-methyl-p-methoxybenzylamine (II; R1=p—CH3O—C6H4; R2=C2H5; R3=CH3; m=1; R4=CH(CH2)2; R5=3,4 Cl2—C6H3; Q=—CH=CH—)

In accordance with example 10 and from the intermediate F.6 and cyclopropanecarbonyl chloride.
y.=91% (chromatography).
TLC: 0.60; S.L.
NMR: 0.00–0.10 (m, 2H); 0.30–0.60 (m, 2H); 0.60–1.00 (m, 4H); 1.60–2.00 (m, 2H); 2.20–2.50 (m, 5H); 2.80 (d, 2H); 3.80 (s, 3H); 6.00–6.50 (m, 2H); 6.70–7.50 (m, 7H).

EXAMPLE 16

α-(3',4'-Dichloro)cinnamyl-N-cyclopropyl-methyl-α-ethyl-N-methyl-p-chlorobenzylamine (II; R1=p—Cl—C6H4; R2=C2H5; R3=CH3; m=1; R4=CH(CH2)2; R5=3,4 Cl2—C6H3; Q=—CH=CH—)

In accordance with example 10 and from the intermediate F.7 and cyclopropanecarbonyl chloride.
y.=57% (chromatography).
TLC: 0.45; S.K.
NMR: 0.00–0.15 (m, 2H); 0.30–0.60 (m, 2H); 0.60–1.00 (m, 4H); 1.55–2.05 (m, 2H); 2.20–2.50 (m, 5H); 2.80 (d, 2H); 5.90–6.50 (m, 2H); 6.90–7.50 (m, 7H).

EXAMPLE 17

α-(3',4'-Dichloro)cinnamyl-N-cyclopropyl-methyl-α-ethyl-N-methyl-m-trifluoromethyl-benzylamine (III; R1=m—F3C—C6H4; R2=C2H5; R3=CH3; m=1; R4=CH(CH2)2; R5=3,4 Cl2—C6H3; Q=—CH=CH—)

In accordance with example 10 and from the intermediate F.8 and cyclopropanecarbonyl chloride.
y.=64%.
m.p.=66° C. (hexanes).
TLC: 0.70; S.K.
NMR: 0.00–0.15 (m, 2H); 0.30–0.60 (m, 2H); 0.60–0.90 (m, 4H); 1.70–2.10 (m, 2H); 2.35 (d, 2H); 2.50 (s, 3H); 2.85 (d, 2H): 5.90–6.50 (m, 2H); 7.00–7.90 (m, 7H).

EXAMPLE 18

N-Cyclopropylmethyl-α-ethyl-N-methyl-α-(3',4',5'-trimethoxy)cinnamyl-benzylamine (III; R1=C6H5; R2=C2H5; R3=CH3; m=1; R4=CH(CH2)2; R5=3,4,5 (CH3O)3—C6H2; Q=—CH=CH—)

76.0 ml of a 3M ethereal solution of ethylmagnesium bromide (227 mmol) are introduced into a reactor in the absence of moisture and under a nitrogen atmosphere.

20.5 g (50.4 mmol) aminonitrile IX described in preparation G.1 dissolved in 65 ml THF, dehydrated over a molecular sieve, are then added at a temperature between 20° and 30° C.

The mixture is stirred for 3 hours at room temperature and then introduced into 260 ml of a saturated aqueous solution of ammonium chloride, without exceeding 10° C.

The aqueous phase is discarded and the organic phase is extracted 3 times with a 2N solution of hydrochloric acid.

The combined hydrochloric phases are rendered alkaline with a concentrated solution of sodium hydroxide and then extracted with ether. The ethereal phases are combined, washed with water and then dehydrated over Na2SO4.

After removal of the ether by distillation, the product is purified by chromatography.
weight: 11.0 g.
y.=53%.
TLC: 0.40; S.L.
NMR: 0.00–0.10 (m, 2H); 0.30–0.60 (m, 2H); 0.60–0.90 (m, 4H); 1.70–2.10 (m, 2H); 2.30–2.50 (m, 5H); 2.85 (d, 2H); 4.85 (s, 9H); 5.90–6.55 (m, 2H); 6.60 (t, 2H); 7.10–7.60 (m, 5H).

EXAMPLE 19

α-Cinnamyl-N-cyclopropylmethyl-α-ethyl-N-methyl-α-3,4,5-trimethoxy)benzylamine (III;
R1=3,4,5(CH3O)3—C6H2; R2=C2H5; R3=CH3; m=1; R4=CH(CH2)2; R5=C6H5; Q=—CH=CH—)

The compound is prepared in accordance with the operating method of the above example by reaction of ethylmagnesium bromide with α-amino-α-cinnamyl-N-cyclopropylmethyl-N-methyl-(3,4,5-trimethoxy)-phenylacetonitrile.

y.=47%.
b.p./0.025=175° C.
TLC=0.30; S.C.
NMR: 0.20–0.60 (m, 4H); 0.90 (m, 4H); 1.90 (q, 2H); 2.40 (m, 2H); 2.50 (s, 3H); 2.80 (d, 2H); 3.90–4.00 (m, 9H); 6.30–6.70 (m, 2H); 6.85 (s, 2H); 7.20–7.40 (m, 5H).
Anal. (C26H35NO3) C, H, N, O.

This operating method is used on the intermediates IX G.2 to G.7 with ethylmagnesium bromide to give the compounds of the formula III according to the invention of examples 20 to 25.

EXAMPLE 20

α-Cinnamyl-N-cyclopropylmethyl-α-ethyl-N-methyl-2-furfurylamine (III; R1=2-furyl; R2=C2H5; R3=CH3; m=1; R4=CH(CH2)2; R5=C6H5; Q=—CH=CH—)

From the aminonitrile G.2
Yellow oil.
TLC=0.55; S.C.
NMR: 0.10–0.60 (m, 5H); 0.90 (t, 3H); 1.90 (q, 2H); 2.30 (d, 2H); 2.40 (s, 3H); 2.80–2.90 (m, 2H); 6.20–6.60 (m, 4H); 7.30–7.40 (m, 6H).
Anal. (C21H27NO) C, H, N, O.

EXAMPLE 21

α-Cinnamyl-N-cyclopropylmethyl-α-ethyl-N-methyl-2-thiophenemethylamine (III; R1=2-thienyl; R2=C2H5; R3=CH3; m=1; R4=CH(CH2)2; R5=C6H5; Q=—CH=CH—)

From the aminonitrile G.3
Yellow oil.
b.p./0.25=160° C.
TLC=0.25; S.O.
NMR: 0.05–0.55 (m, 5H); 1.90 (m, 5H); 2.30 (d, 2H); 2.50 (s, 3H); 2.90 (d, 2H); 6.10–6.60 (m, 2H); 7.00–7.10 (m, 2H); 7.20–7.30 (m, 6H).
Anal. (C21H27NS) C, H, N, S.

EXAMPLE 22

α-Cinammyl-N-cyclopropylmethyl-α-ethyl-N-methyl-3-thiophenemethylamine (III; R1=3-thienyl; R2=C2H5; R3=CH3; m=1; R4=CH(CH2)2; R5=C6H5; Q=—CH=CH—)

From the aminonitrile G.4
Yellow oil.
b.p./0.025=140° C.
TLC=0.45; S.A.
NMR: 0.10–0.55 (m, 4H); 0.70 (s, 1H); 0.75 (t, 3H); 1.85 (q,2H); 2.25 (d, 2H); 2.40 (s, 3H); 6.00–6.50 (m, 2H); 7.00–7.40 (m, 8H).
Anal. (C21H27NS) C, H, N, S.

EXAMPLE 23 trans-N-Cyclopropylmethyl-α-ethyl-N-methyl-α-(2-phenyl-1-cyclopropylmethyl)-2-furfurylamine (III; R1=2-furyl; R2=C2H5; R3=CH3; m=1; R4=CH(CH2)2; R5=C6H5; Q=cyclopropane-1,2-diyl)

From the aminonitrile G.5
Maroon oil.
TLC=0.45; S.C.
NMR: 0.40–0.95 (m, 11H); 1.20–1.70 (m, 2H); 1.95 (m, 3H); 2.15 (m, 2H); 2.35 (s, 3H); 6.05 (m, 1H); 6.35 (m, 1H); 6.85–7.35 (m,6H).
Anal. (C22H29NO) C, H, N, O.

EXAMPLE 24 trans-N-Cyclopropylmethyl-α-ethyl-N-methyl-α-(2-phenyl-1-cyclopropylmethyl)-2-thiophenemethylamine (III; R1=2-thienyl; R2=C2H5; R3=CH3; m=1; R4=CH(CH2)2; R5=C6H5; Q=cyclopropane-1,2-diyl)

From the aminonitrile G.6
Maroon oil.
TLC=0.45; S.A.
NMR: 0.10 (m, 2H); 0.40–0.50 (m, 2H); 0.80–0.95 (m, 5H); 1.30 (s, 1H); 1.50–1.90 (m,2H); 2.00–2.10 (m, 4H); 2.30 (d, 2H); 2.45 (s, 3H); 6.80–7.25 (m, 8H).
Anal. (C22H29NS) C, H, N, S.

EXAMPLE 25 trans-N-Cyclopropylmethyl-α-ethyl-N-methyl-α-(2-phenyl-1-cyclopropylmethyl)-3-thiophenemethylamine (III; R1=3-thienyl; R2=C2H5; R3=CH3; m=1; R4=CH(CH2)2; R5=C6H5; Q=cyclopropane-1,2-diyl)

From the aminonitrile G.7
Maroon oil.
TLC=0.75; S.D.
NMR: 0.05–0.15 (m, 1H); 0.25–0.55 (m, 2H); 0.60–1.10 (m, 7H); 1.30–1.75 (m, 2H); 1.75–2.10 (m, 4H); 2.15–2.35 (m, 2H); 2.40 (s, 3H); 6.85–7.40 (m, 8H).
Anal. (C22H29NS) C, H, N, S.

The toxicological and pharmacological tests carried out with the compounds of the above examples 1 to 25 demonstrate their low toxicity and likewise, in mice, their ability to inhibit convulsions induced by picrotoxin.

This property suggests usefulness of the products according to the invention as psychotropic agents in the treatment of neuropsychic conditions.

In addition, and with the aim of continuing the study of their pharmacological properties, bonding affinities to mu, delta and kappa receptors have been studied "in vitro", as has the bonding affinity to sigma receptors.

The results of the studies performed reveal, for the compounds according to the invention, a particular bonding affinity for sigma receptors, which is more obvious when, in the compound, R1 is a phenyl radical or a 2-thienyl radical and R5 is phenyl.

This property suggests an antipsychotic activity for the compounds according to the invention, the correlation having being proposed recently by Brian L. Largent and coll. (Eur. J. of Pharmacol. 155 (1988) p. 345–347), who find that compounds which vary in their structure but are all potentially antipsychotic have a common property which comprises an "in vitro" affinity for sigma receptors.

Equally, but "in vivo" in rats, the cycloalkylalkylamines (I) antagonize the amnesic phenomena caused by scopolamine and inhibit at the gastro-duodenal level ulcers caused by administration of cysteamine. This activity is associated with the property of the products of increasing alkaline duodenal secretion in anaesthetized animals. All of these properties have been concretized by the studies performed and their results presented in this report render the compounds according to the invention useful for the prevention and treatment of asthenias and disorders of a neurological and/or mental type, as well as the treatment of various dysfunctions of the gastro-intestinal tract.

The studies which demonstrate the properties of the products according to the invention and the results obtained are reported below:

a) the toxicity of products according to the invention is investigated in mice by approximate determination of their LD50, which is the lethal dose causing 50% deaths in the animals under the conditions of the experiments. The study is carried out on groups of four "Swiss" male mice which weight about 20 g and have been fasted the day before the study.

Each determination is carried out with four doses corresponding respectively to oral administration of 100, 300, 600 and 1,000 mg product, expressed in the form of the base, per kg animal.

It is found in this study that the products according to the invention have an acute toxicity corresponding to an LD50 greater than or equal to 1,000 mg/kg. In exceptional cases this toxicity may be about 600 mg/kg.

b) The psychotropic properties of the compounds were determined by the protection from convulsions induced by picrotoxin in mice, which was realized in accordance with a method derived from that of Krall and coll., "Epilepsia", 1978, 19, p. 409-428.

The administration of picrotoxin to animals causes a convulsive attack characterized by a myoclonic extension syndrome followed by extension of the limbs leading to death of the animals. Certain substances, in particular those which act on the GABA/benzodiazepine/Cl-ionophor complex, provide protection of the animals from these convulsive attacks.

In practice, the study is carried out on groups of 10 "Swiss" male mice weighing about 20 g, to which the product under investigation is administered in aqueous solution either intraperitoneally (i.p.) or orally (p.o.).

An intraperitoneal injection of a solution of picrotoxin in an amount of 24 mg/kg in a volume of 0.2 ml per animal is then performed, either 30 minutes after intraperitoneal administration of the product or 60 minutes after oral administration of the product, the dose of the product injected in this way causing a clonic attack which leads to death of the untreated animals. Under the conditions of the test, suppression of the tonic extension phase is found in the animals treated.

The results are expressed:
either as the percentage of animals protected from this phase under the action of 50 mg/kg compound under investigation administered i.p. or 100 mg/kg p.o.,
or in the ED50 for each of these groups, which is the effective dose of the compound under investigation expressed in mg/kg which protects 50% of animals from this extension phase, the significance value of the results generally being indicated in the following manner:

\* Result significant at p.<0.05
\*\* Result significant at p.<0.01
\*\*\* Result highly significant at p.<0.001.

The results of the study are reported for the products II and III of the general formula I according to the invention in table 1 which follows, and demonstrate the protective activity of the compounds according to the invention studied for the two administration routes.

TABLE 1

| | Inibition of convulsions induced by picrotoxin | |
|---|---|---|
| Example | i.p.: % prot. or ED50 | p.o.: % prot. or ED50 |
| 2 | NT | 90%*** |
| 8 | NT | ED50 = 53.6 |
| 9 | 90%*** | NT |
| 10 | 50%* | NT |
| 11 | 70%** | NT |
| 13 | ED50 = 32.5 | ED50 = 64.4 |
| 16 | NT | 60%** |
| 20 | NT | 60%** |
| 21 | 50%* | NT |
| 23 | 50%* | NT |
| 24 | 50%* | 50%* |
| 25 | 50%* | 50%* |

N.T. not tested c) The "in vitro" study of the affinity of the compounds for sigma receptors is performed in accordance with the technique described by Largent B. L. and coll. in J. Pharmacol. Exp. Ther. 238, 1986, p. 739-748, the principle of which is competition between the respective affinities of the product under investigation and that of (+)[3H]SKF10,047, which is the radioactive ligand characteristic of sigma receptors of the cerebral membranes of the guinea-pig used in this study.

The test is carried out by incubating solutions of suitable concentrations of the products with standard samples of membranes and determining, after filtration, the residual radioactivity of the solution.

The results are processed with the aid of a data processing system equipped with suitable software in order to calculate the IC50 of the product under investigation, which is, in this case, the nanomolar concentration of solution capable of inhibiting 50% of the bonds between the radioactive ligand and the sigma receptors of the membranes used.

The results are shown in table 2 which follows and, for reference, those obtained with ditolylguanidine (DTG), which is regarded as a selective ligand of great affinity for sigma receptors (Stephen G. Holtzman. J. Pharm. Exp. Ther. Vol. 248, no. 3, 1989, p. 1054–1062) are also shown. However, this compound, the excessive toxicity of which has been demonstrated on animals, is used solely as a pharmacological reagent.

TABLE 2

| Bonding affinity of the compounds according to the invention to sigma receptors | |
|---|---|
| Compounds under investigation example | IC50 (nmol) |
| 3 | 368 |
| 6 | 246 |
| 7 | 32 |
| 8 | 21 |
| 9 | 24 |
| 10 | 13 |
| 11 | 102 |
| 12 | 50 |
| 21 | 95 |
| 24 | 29 |

TABLE 3

Affinity of the products according to the invention to sigma receptors compared with their affinity to mu, delta, kappa and PCP receptors

| Compounds under investigation example | mu rec. | delta rec. | kappa rec. | sigma rec. | PCP rec. |
|---|---|---|---|---|---|
| 7 | >99999 | 51750 | 72800 | 32 | 50800 |
| 8 | 2040 | 7550 | 1520 | 21 | 25900 |
| 9 | 15800 | 82800 | 6200 | 24 | 3670 |
| 10 | 6320 | 67900 | 23800 | 13 | 4590 |
| 11 | 6580 | 41600 | 5140 | 210 | 7100 |
| 12 | 7180 | 85600 | 6280 | 50 | NT |
| 13 | 10200 | 9370 | 8680 | 337 | 10500 |
| 14 | 34200 | >99999 | 76000 | 669 | 14150 |
| 21 | 1542 | 7387 | 1196 | 95 | 6280 |
| 24 | 3024 | 57043 | 9095 | 29 | NT |
| DTG | 3970 | 33200 | 6490 | 103 | 6750 |

N.T.: not tested

TABLE 2-continued

Bonding affinity of the compounds according to the invention to sigma receptors

| Compounds under investigation example | IC50 (nmol) |
|---|---|
| DTG | 103 |

These results demonstrate that the benzylamines according to the invention have an affinity for sigma receptors of the same order of size and sometimes almost 10 times greater than that of DTG on the same receptors.

These affinities, together with low toxicities of the cycloalkylalkylamines (I), demonstrate their superiority in comparison with DTG.

The specificity of the affinity of the compounds for sigma receptors is demonstrated by a comparative study of the affinity of the products to mu, delta and kappa opium receptors, and also to phencylcylidine (PCP) receptors, which are receptors which are recognized as being involved as mediators in the effect of psychomimetic drugs (Eric J. Simon—"Opiates receptor binding in Drug Research" p. 183-199 in "Receptor Binding in Drug Research"—Ed. Robert A. O'Brien-Marcel Dekker—1986, and also Brian L. Largent and coll. in Eur. J. of Pharmacol. 155 (1988) p. 345-347.

The "in vitro" study of the affinity of the compounds according to the invention for the three opium receptors is carried out in accordance with the technique described by F. Roman and coll. in J. Pharm. Pharmacol. 1987, 39, p. 404–407 and the study of the affinity for PCP receptors is carried out in accordance with the technique described by Vignon J. and coll. in "Brain Res." 1983; 280, p. 194–7 and 1986; 378, p. 133–41.

The results shown in table 3 are, for each receptor studied, expressed in IC50, which are the nanomolar concentrations of the dissolved products which are capable of inhibiting 50% of the bonds between the specific radioactive ligand to the receptor under consideration.

A specificity of sigma affinity is evident for the preferred compounds according to the invention.

Thus, if the value of 1 is attributed to the IC50 of sigma affinity, the relative values of the IC50 to other receptor are calculated for the compounds of examples 7, 8, 9, 10 and 12, the sigma affinity of which is the greatest. These values are compared with those obtained with the DTG used as the reference compound.

| Compounds under investigation example | mu rec. | delta rec. | kappa rec. | sigma rec. | PCP rec. |
|---|---|---|---|---|---|
| 7 | >1000 | 1617 | 2275 | 1 | 1587 |
| 8 | 97 | 359 | 72 | 1 | 1233 |
| 9 | 658 | 3491 | 258 | 1 | 153 |
| 10 | 486 | 5223 | 1830 | 1 | 353 |
| 12 | 143 | 1712 | 125 | 1 | — |
| 24 | 104 | 1967 | 314 | 1 | — |
| DTG | 38 | 322 | 63 | 1 | 65 |

This method of expression demonstrates that under the operating conditions described, the preferred compounds according to the invention have an affinity for the sigma receptors which is about 100 times greater than that determined for the other receptors studied, and in several cases more than 1,000 times greater.

Compared with the products according to the invention, ditolylguanidine (DTG), the stated reference compound with selectivity for sigma receptors, shows values which are sometimes close to but always less than the values calculated for the preferred products according to the invention, whatever the receptor.

This particular expression of the study illustrates the remarkable selectivity of the affinity of the products according to the invention for sigma receptors.

d) The ability of the cycloalkylalkylamines (I) to antagonize amnesia caused in animals by scopolamine is demonstrated by the passive avoidance test performed on mice in accordance with a method described by Lenegre and coll.; in principle, it comprises using a box with two compartments, the smaller of which is illuminated and the larger of which is dark and fitted with a system which delivers a low intensity electric current through the floor of the apparatus.

The animal is introduced into the illuminated compartment, and when it moves to the dark compartment it receives an electric current (0.35 mA) through the base until it returns to the illuminated compartment, from where it is then removed.

After 24 hours, the operation is repeated. The mouse is replaced in the apparatus and it avoids entering into the dark compartment. The time which elapses before passage into this compartment is recorded; under the conditions of the experiment, the efficacy of the compounds under investigation in antagonizing the amnesic effect of scopolamine, which is administered intraperitoneally in an amount of 1 mg/kg 30 minutes before the animal is first introduced into the apparatus, can be evaluated.

In control mice which have received only scopolamine, the time elapsed before passage after 24 hours is remarkably lower than that observed in the untreated animals. In the animals which have received both scopolamine and the product under investigation, this time is notably longer under the antiamnesic action of the active compounds.

The study of the products according to the invention by this method is performed on groups of 18 mice and the products are administered orally on the first day in an amount of 0.25 mg/kg 30 minutes before administration of scopolamine i.p.

The results are shown in table 4 and are expressed as the percentage antagonistic effect on the amnesia caused by scopolamine, the antagonism being determined from the latency period demonstrated by the animals in the second test after 24 hours in respect of entering the dark compartment.

TABLE 4

| Activity of the products according the invention on the amnesia caused in mice by scopolamine | |
|---|---|
| Compounds under investigation (0.25 mg/kg) | % antagonism of the amnesia |
| 7 | 56% |
| 9 | 76% |
| 10 | 76% |
| 11 | 38% |
| 12 | 98% |
| PIRACETAM (2048 mg/kg) | 109% |

These results are conclusive of an activity of the products according to the invention at a low dose, and in particular of the compounds of examples 9, 10 and 12.

In this test, the standard reference substance which provides evidence that the test is proceeding properly is piracetam. In an amount of 2,048 mg/kg p.o., which is a considerable pharmacological dose and inapplicable to pharmaceutical ends, it causes antagonism of the amnesia of a value of about 100%.

e) The activity of the compounds according to the invention on the gastrointestinal tract was demonstrated in rats by their ability to inhibit gastroduodenal ulcers caused by administration of cysteamine. This activity is set in relation to the capacity of the products to cause an increase in the alkaline secretion in the duodenum in anaesthetized animals.

The inhibitory activity on gastro-duodenal ulcers caused in rats by cysteamine was demonstrated in accordance with a technique described by Robert and coll., in "Digestion", 1974, 11, p. 199-211.

In this test, groups of 6 Wistar female rats with an average weight of 200 g receive a subcutaneous injection of cysteamine hydrochloride in an amount of 400 mg/kg. The products under investigation are administered orally or subcutaneously 1 h or, respectively, 30 minutes before the ulcerogenic agent.

Ten hours thereafter, the rats are sacrificed by elongation and their stomach and duodenum are removed, rinsed with physiological solution and mounted on a card. The presence of ulcers in the antro-pyloric--duodenal zone is examined and their area, expressed in $mm^2$, is evaluated by multiplying the two main perpendicular axis of the lesion. Statistical analysis of the results is performed with the aid of the Student test for the ulcerated areas in comparison with a control group receiving only excipient.

The results presented in table 5 are expressed in ED50 of ulceration scores, which are the effective doses, expressed in mg/kg product, which cause inhibition of 50% of the ulcerations caused by cysteamine.

TABLE 5

| Inhibitory activity on the gastro-duodenal ulcers caused by cysteamine | |
|---|---|
| Product under investigation example | ED50 - ulceration scores mg/kg |
| 7 | 10.5 |
| 9 | 26.2 |
| 10 | 5.0 |
| 12 | 12.2 |
| 21 | 48.2 |
| 24 | 45.7 |

The activity of the products on alkaline duodenal secretion in rats is studied in accordance with a technique described by FLEMSTROM and coll. Gastroenterology, 1983, 84, p. 787-794.

The test comprises determination every 10 minutes, for 3 hours and in situ, of the alkaline secretion of a duodenal segment 12 mm in length, with no Brunner glands and situated 2 cm from the pylorus.

The study is performed on male rats of about 350 g previously anaesthetized, in which the duodenal segment chosen is cannulated by 2 glass tubes in accordance with the technique described by the author, and in which a luminal perfusate consisting of 5 ml isotonic NaCl solution is maintained at 37° C.

The variations in the intraluminal alkaline secretion are measured by pHmetry every 10 minutes by means of an automated system maintaining a constant pH of 7.4 by in situ addition of a 0.04 N solution of hydrochloric acid. Fifty minutes after the start of the experiment, the products under investigation are administered intravenously or intraarterially in an amount of 1 mg/kg and the volume of hydrochloric acid introduced, which is a reflection of the in situ increase in alkaline secretion, is measured every 10 minutes for 3 hours with respect to the start of the experiment, that is to say for 130 minutes after injection of the product under investigation.

The following are determined for each product:

a) The maximum increase in secretion in microeq/cm/h under the action of the drug, taking into account the basal secretion of the same animals observed for 50 minutes before administration of the product.

b) The increase in the area under the curve (AUC) in the interval from 1 h to 2 h of the experiment over the alkaline flow rate of the treated animals compared with that of the control animals.

These increases are representative of the promoting activity on alkaline secretion.

The results are shown in table 6, which follows, for the products (I) according to the invention administered intravenously in an amount of 1 mg/kg.

TABLE 6

Activity of the products according to the invention on alkaline duodenal secretion in anaesthetized rats

| Product under investigation example | Increase in secretion micro-eq/cm/h | Increase AUC 1 2 h |
|---|---|---|
| 7 | 6.0 | 52.8 |
| 9 | 10.0 | 97.6 |
| 10 | 7.5 | 66.2 |
| 12 | 7.0 | 41.6 |

These tests performed at the gastroduodenal level in rats demonstrate that the products according to the invention have a convincing inhibitory activity on ulcers such as those caused by cysteamine. A probable relationship between this inhibitory activity and the property of the same products according to the invention of increasing alkaline duodenal secretion is confirmed.

These pharmacological properties, together with the low toxicity of the compounds according to the invention, suggest their usefulness in the form of medicaments for preventive and curative treatments of conditions of a neurological and/or mental order in general, such as, for example, depressive states, memory and/or behavioral disturbances, schizophrenia, Alzheimer's disease, Parkinson's disease and senile dementia.

The cycloalkylalkylamines (I) according to the invention are likewise suitable for treatment of dysfunctions of the gastrointestinal tract in general, such as, for example, peristalsis and motoricity disturbances, gastrooesophageal and gastroduodenal reflux phenomena and also gastric and gastroduodenal ulcerations.

The unit does used are usually between 1 and 500 mg, and more particularly between 5 and 200 mg product, depending on the nature and the severity of the condition to be treated. The daily therapeutic doses can be divided into several administrations and are between 5 and 2,000 mg product per day. A daily dosage of 50 to 500 mg product per day divided into two to four administrations is generally sufficient.

The products according to the invention are administered to patients to be treated in the form of medicaments of a suitable nature for the condition to be treated. The medicamentous preparations will be, as nonlimiting examples, tablets, coated tablets, capsules, powders, solutions, suspensions, gels or suppositories, depending on the case. The pharmaceutical forms are prepared from the products in the form of the base or their salts and in accordance with the methods usually employed in this industry.

In medicamentous forms of a solid nature, the active principle generally makes up 5 to 90% by weight of the total finished form, and the medicaments thus make up 95 to 10%. For liquid forms, which can be considered as such, the amount of active principle is between 0.1 and 10% by weight of the finished form, and the excipient can thus make up 99.9 to 90% by weight of this form.

The formulation and preparation of isotonic injectable solutions, of tablets and of gels for oral administration are given by way of example.

Isotonic injectable solution

Formula:

| | |
|---|---|
| Active substance of example 10 (hydrochloride) | 10 mg |
| Sodium chloride | 9 mg |
| Distilled water in an amount sufficient for | 1.0 ml |

Preparation:

The isotonic solution is divided into ampoules of suitable volume which, after sealing, are sterilized by thermal means which are known per se, or the solution is sterilized by filtration and divided amongst ampoules which are then sealed, all the operations being performed under a sterile atmosphere.

In this latter case, 1% benzyl alcohol is preferably added to the formula described as a bacteriostatic agent, that is to say 10 mg of this alcohol per ml solution.

Tablets

Formula

| | |
|---|---|
| Active substance of example 9 (hemimaleate) | 10.0 to 50.0 mg |
| Polyvinylpyrrolidone | 20.0 mg |
| Carboxymethyl-starch | 8.0 mg |
| Magnesium stearate | 2.0 mg |
| Colloidal silica | 0.4 mg |
| Lactose in an amount sufficient for | 200.0 mg |

Preparation

The active principle is mixed with lactose and the mixture is then granulated with polyvinylpyrrolidone in solution. The granules are dried and sieved over a screen of mesh 1 mm. The carboxymethyl-starch is mixed with the colloidal silica and the mixture is then added to the granules. The components are then mixed intimately with the magnesium stearate and the mixture is subsequently pressed to tablets in an amount of 200.0 mg per tablet.

Gel

Formula

| | |
|---|---|
| Active substance of example 9 (hemimaleate) | 0.20 to 0.60 g |
| Hydroxypropylcellulose | 2.00 g |
| Sodium saccharinate | 0.01 g |
| 70% (w/v) sorbitol syrup | 25.00 g |
| Natural strawberry aroma | 0.50 g |
| Preservative | 0.10 g |
| Purified water in an amount sufficient for | 100.00 g |

Preparation:

The preservatives and the sodium saccharinate are dissolved in the water and the hydroxypropylcellulose dispersant is then added, while stirring. Stirring is maintained until a gel is obtained, to which the sorbitol syrup and then finally the aroma are added, with constant stirring.

We claim:

1. N-cycloalkylalkylamine having the formula

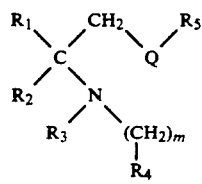

(I)

wherein $R_1$ is an aromatic heterocyclic radical selected from the group consisting of furyl and thienyl, $R_2$ is lower alkyl,
$R_3$ is hydrogen or lower alkyl,
$R_4$ is cycloalkyl—$CH(CH_2)_n$ wherein n is an integer ranging from 2 to 5 and wherein a carbon atom of $R_4$ optionally carries a radical $R_X$ wherein $R_X$ is lower alkyl or phenyl,
$R_5$ is phenyl optionally mono-, di- or trisubstituted by halogen or lower alkoxy,
Q represents ethylene-1,2-yl group —CH=CH— or cyclopropane-1,2-diyl group

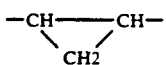

and m has a value of 1 or 2,
the acid addition salt thereof and the optically active form thereof.

2. The N-cycloalkylalkylamine of claim 1 wherein $R_1$ is 2-furyl.

3. The N-cycloalkylalkylamine of claim 1 wherein $R_1$ is 2-thienyl.

4. The N-cycloalkylalkylamine of claim 1 wherein $R_1$ is 3-thienyl.

5. The N-cycloalkylalkylamine of claim 1 wherein $R_5$ is phenyl.

6. The N-cycloalkylalkylamine of claim 1 wherein $R_2$ is ethyl.

7. The N-cycloalkylalkylamine of claim 1 wherein $R_3$ is methyl.

* * * * *